United States Patent
Kim et al.

(10) Patent No.: US 10,702,185 B2
(45) Date of Patent: Jul. 7, 2020

(54) ELECTRONIC DEVICE AND BODY COMPOSITION ANALYZING METHOD

(71) Applicant: SAMSUNG ELECTRONICS CO., LTD., Suwon-si, Gyeonggi-do (KR)

(72) Inventors: Young Hyun Kim, Suwon-si (KR); Konstantin Pavlov, Moscow (RU); Jee Hoon Lee, Seoul (KR); Nam Seok Chang, Hwaseong-si (KR)

(73) Assignee: SAMSUNG ELECTRONICS CO., LTD., Suwon-si, Gyeonggi-do (KR)

( * ) Notice: Subject to any disclaimer, the term of this patent is extended or adjusted under 35 U.S.C. 154(b) by 327 days.

(21) Appl. No.: 15/896,353

(22) Filed: Feb. 14, 2018

(65) Prior Publication Data

US 2018/0235507 A1 Aug. 23, 2018

(30) Foreign Application Priority Data

Feb. 17, 2017 (KR) .................. 10-2017-0021745

(51) Int. Cl.
*A61B 5/00* (2006.01)
*A61B 5/053* (2006.01)
(Continued)

(52) U.S. Cl.
CPC .......... *A61B 5/0537* (2013.01); *A61B 5/4869* (2013.01); *A61B 5/7203* (2013.01);
(Continued)

(58) Field of Classification Search
CPC ..... A61B 5/053; A61B 5/0531; A61B 5/0535; A61B 5/0537; A61B 5/4869;
(Continued)

(56) References Cited

U.S. PATENT DOCUMENTS 6,532,384 B1 3/2003 Fukuda
6,675,041 B2 1/2004 Dickinson
(Continued)

FOREIGN PATENT DOCUMENTS

JP 2001-212101 8/2001
KR 10-2005-0027368 3/2005
(Continued)

OTHER PUBLICATIONS

Extended Search Report dated Aug. 9, 2018 in counterpart European Patent Application No. 18157196.9.
(Continued)

*Primary Examiner* — Eric F Winakur
*Assistant Examiner* — Maria E Conneran
(74) *Attorney, Agent, or Firm* — Nixon & Vanderhye, P.C.

(57) ABSTRACT

An electronic device includes a memory storing profile information, at least one first electrode, at least one second electrode, and a processor connected to the at least one first electrode and the at least one second electrode. The processor is configured to determine a frequency of at least one signal for measuring body composition, based on the profile information, output a synthesis signal obtained by synthesizing the at least three signals to a body of the user through the at least one first electrode, wherein the synthesis signal includes a signal corresponding to the determined frequency and the at least three signals have different frequencies, receive the synthesis signal passing through the body of the user, through the at least one second electrode, measure body impedance of the user based on the received synthesis signal, and measure the body composition of the user based on the body impedance.

20 Claims, 19 Drawing Sheets

(51) Int. Cl.
    *A61B 5/024*         (2006.01)
    *A61B 5/0428*       (2006.01)
    *A61B 5/117*        (2016.01)

(52) U.S. Cl.
    CPC ........ *A61B 5/7228* (2013.01); *A61B 5/02438* (2013.01); *A61B 5/04284* (2013.01); *A61B 5/117* (2013.01); *A61B 5/6802* (2013.01); *A61B 5/6898* (2013.01)

(58) Field of Classification Search
    CPC ... A61B 5/4872; A61B 5/4875; A61B 5/4881; A61B 5/4878
    USPC .......................................................... 600/547
    See application file for complete search history.

(56) References Cited

U.S. PATENT DOCUMENTS

| | | | |
|---|---|---|---|
| 7,340,295 B2 * | 3/2008 | Shiokawa | A61B 5/0537 600/300 |
| 7,502,643 B2 | 3/2009 | Farringdon et al. | |
| 8,369,936 B2 | 2/2013 | Farringdon et al. | |
| 8,459,094 B2 | 6/2013 | Yanni | |
| 8,836,345 B2 * | 9/2014 | Chetham | G01R 1/18 324/649 |
| 2005/0054938 A1 | 3/2005 | Wehman et al. | |
| 2005/0054944 A1 | 3/2005 | Nakada et al. | |
| 2005/0113703 A1 | 5/2005 | Farringdon et al. | |
| 2007/0129944 A1 | 6/2007 | Luan et al. | |
| 2008/0125700 A1 | 5/2008 | Moberg et al. | |
| 2008/0139952 A1 | 6/2008 | Kuroda et al. | |
| 2008/0161707 A1 | 7/2008 | Farringdon et al. | |
| 2008/0171943 A1 | 7/2008 | Farringdon et al. | |
| 2008/0177193 A1 | 7/2008 | Farringdon et al. | |
| 2008/0183082 A1 | 7/2008 | Farringdon et al. | |
| 2008/0183090 A1 | 7/2008 | Farringdon et al. | |
| 2008/0221805 A1 * | 9/2008 | Andrews | A61B 5/00 |
| 2010/0249642 A1 * | 9/2010 | Cha | A61B 5/0537 600/547 |
| 2010/0286532 A1 | 11/2010 | Farringdon et al. | |
| 2011/0015504 A1 | 1/2011 | Yoo | |
| 2011/0054343 A1 | 3/2011 | Chetham et al. | |
| 2014/0094707 A1 | 4/2014 | Farringdon et al. | |
| 2014/0188414 A1 * | 7/2014 | Jeong | H01M 8/04649 702/63 |
| 2014/0221849 A1 | 8/2014 | Farringdon et al. | |
| 2014/0221850 A1 | 8/2014 | Farringdon et al. | |
| 2017/0209066 A1 | 7/2017 | Chetham et al. | |
| 2018/0067154 A1 * | 3/2018 | Cherkassky | G01R 27/02 |

FOREIGN PATENT DOCUMENTS

| | | | |
|---|---|---|---|
| KR | 10-2005-0103355 | 10/2005 | |
| KR | 10-0817272 | 3/2008 | |
| KR | 10-2010-0000856 | 1/2010 | |
| KR | 10-1000467 | 12/2010 | |
| KR | 10-1049020 | 7/2011 | |
| KR | 10-1084554 | 11/2011 | |
| KR | 10-1237308 | 2/2013 | |
| WO | WO-2015123603 A1 * | 8/2015 | A61B 5/053 |

OTHER PUBLICATIONS

Sanchez, B et al: "Paper;On the calculation of the D-optimal multisine excitation power spectrum for broadband impedance spectroscopy measurements; On the calculation of the D-optimal multisine excitation power spectrum for broadband impedance spectroscopy measurements", Measurement Science and Technology, IOP, Bristol, GB, vol. 23, No. 8, Jul. 4, 2012 (Jul. 4, 2012), p. 85702, XP020227277.

* cited by examiner

ELECTRONIC DEVICE AND BODY COMPOSITION ANALYZING METHOD

CROSS-REFERENCE TO RELATED APPLICATION

This application is based on and claims priority under 35 U.S.C. § 119 to a Korean patent application filed on Feb. 17, 2017 in the Korean Intellectual Property Office and assigned Serial number 10-2017-0021745, the disclosure of which is incorporated by reference herein in its entirety.

TECHNICAL FIELD

The present disclosure relates generally to an electronic device that applies a current to a user's body to measure body composition, and a body composition measuring method of the electronic device.

BACKGROUND

With the development of electronic technologies, various types of electronic products are being developed and distributed. In particular, a portable electronic device having a variety of functions, such as a smart phone, a tablet personal computer (PC), and the like have been increasingly distributed.

Recently, there has been a growing interest in health. Also, interest in workouts has been increasing to keep health. As such, the recently developed electronic device may provide various services that manage the health of a user or measure the user's body state, such as heart rate monitoring, body composition analysis, or the like.

A body composition analyzer may sequentially apply signals of various frequencies to a user's body to measure body impedance and may analyze the user's body composition based on the body impedance. As the number of signals increases, the accuracy of body composition measurement may be improved. However, a time required to measure the body composition may increase.

SUMMARY

Example aspects of the present disclosure address at least the above-mentioned problems and/or disadvantages provides at least the advantages described below. Accordingly, an example aspect of the present disclosure is to provide an electronic device that reduces a time required to measure body composition while the accuracy of body composition measurement is maintained, and increases the accuracy of body composition measurement in consideration of a user's body state, lifestyle, or the like, and a body composition measuring method of the electronic device.

In accordance with an example aspect of the present disclosure, an electronic device includes a memory for storing profile information of a user, at least one first electrode, at least one second electrode, and a processor electrically connected to the at least one first electrode and the at least one second electrode. The processor is configured to determine a frequency of at least one among at least three signals for measuring body composition, based on the profile information of the user, to output a synthesis signal to a body of the user through the at least one first electrode, the synthesis signal being obtained by synthesizing the at least three signals, wherein the synthesis signal includes a signal corresponding to the determined frequency and the at least three signals each have different frequencies, to receive the synthesis signal passing through the body of the user, through the at least one second electrode, to measure body impedance of the user based on the received synthesis signal, and to measure the body composition of the user based on the body impedance.

In accordance with an example aspect of the present disclosure, a body composition measuring method of an electronic device includes determining a frequency of at least one among at least three signals for measuring body composition, based on profile information of a user, outputting a synthesis signal to a body, the synthesis signal being obtained by synthesizing the at least three signals, wherein the synthesis signal includes a signal corresponding to the determined frequency and the at least three signals each have different frequencies, measuring body impedance of the user based on a received synthesis signal, and measuring the body composition of the user based on the body impedance.

In accordance with an example aspect of the present disclosure, a non-transitory computer-readable recording medium has recorded thereon a program which, when executed by a processor, causes an electronic device to perform a method. The method includes determining a frequency of at least one among at least three signals for measuring body composition, based on profile information of a user, outputting a synthesis signal to a body, the synthesis signal being obtained by synthesizing the at least three signals to a body, wherein the synthesis signal includes a signal corresponding to the determined frequency and the at least three signals each have different frequencies, receiving the synthesis signal, measuring body impedance of the user based on the received synthesis signal, and measuring the body composition of the user based on the body impedance.

According to various embodiments of the present disclosure, a time required to measure body composition may be reduced as well as improving the accuracy of body composition measurement.

Other aspects, advantages, and salient features of the disclosure will become apparent to those skilled in the art from the following detailed description, which, taken in conjunction with the annexed drawings, discloses various example embodiments of the present disclosure.

BRIEF DESCRIPTION OF THE DRAWINGS

The above and other aspects, features, and attendant advantages of the present disclosure will be more apparent and readily appreciated from the following detailed description, taken in conjunction with the accompanying drawings, in which like reference numerals refer to like elements, and wherein.

Throughout the drawings, it should be noted that like reference numbers are used to depict the same or similar elements, features, and structures.

DETAILED DESCRIPTION

Figure 1:
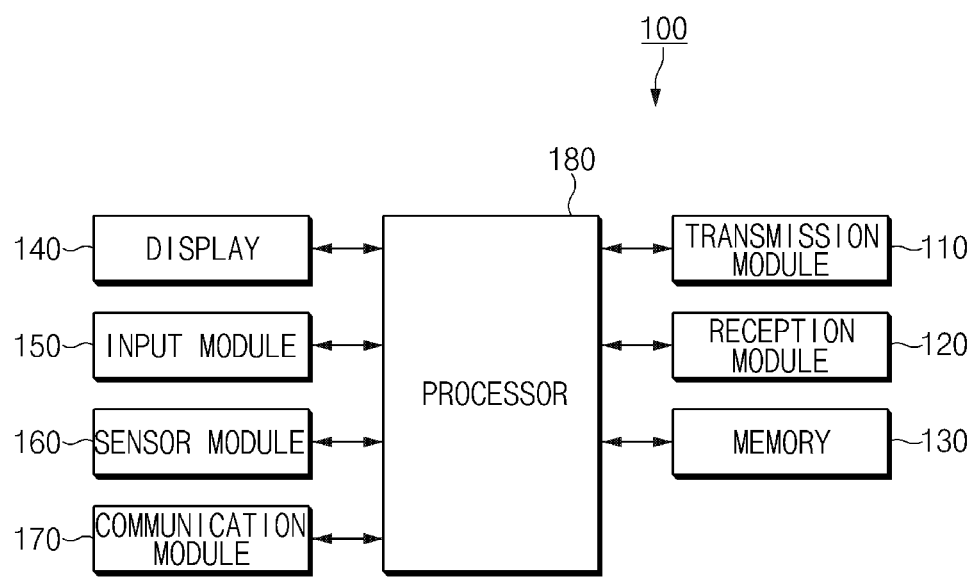
FIG. 1 is a block diagram illustrating an example configuration of an electronic device, according to an example embodiment of the present disclosure.

Hereinafter, various example embodiments of the present disclosure may be described with reference to accompanying drawings. Embodiments and terms used herein are not intended to limit the technologies described in the present disclosure to specific embodiments, and it should be understood that the embodiments and the terms include modifications, equivalents, and/or alternatives of the corresponding embodiments described herein. With regard to description of drawings, similar elements may be marked by similar reference numerals.

The terms of a singular form may include plural forms unless otherwise specified. In the disclosure disclosed herein, the expressions "A or B", "at least one of A or/and B", and the like used herein may include any and all combinations of one or more of the associated listed items. Expressions such as "first," or "second," and the like, may express their elements regardless of their priority or importance and may be used to distinguish one element from another element but is not limited to these components. When an (e.g., first) element is referred to as being "(operatively or communicatively) coupled with/to" or "connected to" another (e.g., second) element, it may be directly coupled with/to or connected to the other element or an intervening element (e.g., a third element) may be present.

According to the situation, the expression "configured to" used herein may be interchangeably used as, for example, the expression "suitable for", "having the capacity to", "designed to", "adapted to", "made to", or "capable of". The expression "a device configured to" may refer to a situation in which the device is "capable of" operating together with another device or other components. For example, a "processor configured to (or set to) perform A, B, and C" may refer, for example, and without limitation, to a dedicated processor (e.g., an embedded processor) for performing a corresponding operation or a generic-purpose processor (e.g., a central processing unit (CPU) or an application processor) which performs corresponding operations by executing one or more software programs which are stored in a memory device.

According to various embodiments of the present disclosure, an electronic device may include at least one of, for example, smartphones, tablet personal computers (PCs), mobile phones, video telephones, electronic book readers, desktop PCs, laptop PCs, netbook computers, workstations, servers, personal digital assistants (PDAs), portable multimedia players (PMPs), Motion Picture Experts Group (MPEG-1 or MPEG-2) Audio Layer 3 (MP3) players, mobile medical devices, cameras, or wearable devices, or the like, but is not limited thereto. According to various embodiments, a wearable device may include at least one of an accessory type of a device (e.g., a timepiece, a ring, a bracelet, an anklet, a necklace, glasses, a contact lens, or a head-mounted-device (HMD)), one-piece fabric or clothes type of a device (e.g., electronic clothes), a body-attached type of a device (e.g., a skin pad or a tattoo), or a bio-implantable type of a device (e.g., implantable circuit), or the like, but is not limited thereto.

According to another embodiment, the electronic devices may be home appliances. The home appliances may include at least one of, for example, televisions (TVs), digital versatile disc (DVD) players, audios, refrigerators, air conditioners, cleaners, ovens, microwave ovens, washing machines, air cleaners, set-top boxes, home automation control panels, security control panels, TV boxes (e.g., Samsung HomeSync™, Apple TVT™, or Google TVT™), game consoles (e.g., Xbox™ or PlayStation™), electronic dictionaries, electronic keys, camcorders, electronic picture frames, or the like, but is not limited thereto.

According to another embodiment, the electronic device may include medical devices (e.g., various portable medical measurement devices (e.g., a blood glucose monitoring device, a heartbeat measuring device, a blood pressure measuring device, a body temperature measuring device, and the like), a magnetic resonance angiography (MRA), a magnetic resonance imaging (MRI), a computed tomography (CT), scanners, and ultrasonic devices), or the like, but is not limited thereto.

FIG. 1 is a block diagram illustrating an example configuration of an electronic device, according to an example embodiment of the present disclosure.

Referring to FIG. 1, an electronic device 100 may include a transmission module (e.g., including transmitting circuitry) 110, a reception module (e.g., including receiving circuitry) 120, a memory 130, a display 140, an input module (e.g., including input circuitry) 150, a sensor module 160, a communication module (e.g., including communication circuitry) 170, and a processor (e.g., including processing circuitry) 180. According to an embodiment, the electronic device 100 may be a device capable of measuring a user's body composition (e.g., body fat, muscle mass, or the like). For example, the electronic device 100 may include, for example, and without limitation, a portable electronic device such as a smartphone, a tablet PC, a wearable device (e.g., a smart watch, or the like) as well as a medical device such as a body composition meter, or the like.

According to an embodiment, the transmission module 110 may include various transmitting circuitry and output a signal (e.g., a current) for measuring the user's body composition. According to an embodiment, the transmission module 110 may include, for example, and without limitation, at least one (e.g., two) first electrode for applying a signal to the user's body. According to an embodiment, in a state where the at least one first electrode contacts the user's body (e.g., palms, fingers, wrists, toes, or the like), the transmission module 110 may output the signal to the user's body.

According to an embodiment, the transmission module 110 may output a synthesis signal obtained by synthesizing at least three signals. For example, the transmission module 110 may output the synthesis signal obtained by synthesizing at least three signals, each having different frequencies.

According to an embodiment, the reception module 120 may include various receiving circuitry and receive a signal for measuring the user's body composition. According to an embodiment, the reception module 120 may include, for example, and without limitation, at least one (e.g., two) second electrode for receiving the signal applied to the user's body. According to an embodiment, in a state where the at least one second electrode contacts the user's body, the reception module 120 may receive a signal that passes through the user's body.

According to an embodiment, the memory 130 may store an application. For example, the memory 130 may store a body composition measuring application, an exercise application, a health managing application, or the like.

According to an embodiment, the memory 130 may store profile information of the user. For example, the profile information of the user may include at least one of the user's height, age, weight, gender, exercise history, food intake history, sleep history, body composition measuring history, body state (e.g., skin moisture, menstrual cycle, or the like), and stress index, or the like, without limitation. According to an embodiment, the memory 130 may update the profile information of the user. According to an embodiment, the memory 130 may, for example, and without limitation, store a look-up table including frequency information of a signal corresponding to the user profile information.

According to an embodiment, the memory 130 may store a signal necessary to measure the body composition of a body. For example, the memory 130 may store a plurality of synthesis signals obtained by synthesizing at least three signals having different frequencies. For another example, the memory 130 may store a sinc signal of a frequency range for measuring body impedance.

According to an embodiment, the display 140 may display a user interface. For example, the display 140 may display a user interface for measuring the body composition.

According to an embodiment, the input module 150 may include various input circuitry and receive a user input. According to an embodiment, the input module 150 may receive the user input to measure the body composition. According to an embodiment, the input module 150 may receive the profile information of the user.

In an embodiment, the input module 150 may include, for example, and without limitation, a touch sensor panel that senses a touch manipulation of the user or a pen sensor panel that senses a pen manipulation of the user, or the like. According to an embodiment, the input module 150 may include a button for sensing a push, rotation, or the like, of the user.

According to an embodiment, for example, the display 140 and the input module 150 may be implemented with a touch screen that is capable of displaying and sensing the touch input at the same time. In the touch screen, a touch sensor panel may be disposed on the display panel.

According to an embodiment, the sensor module 160 may include various sensing circuitry and/or sensors and sense the electronic device 100 or the state of the user. According to an embodiment, the sensor module 160 may include, for example, and without limitation, an acceleration sensor, a gyro sensor, a heart rate monitoring (HRM) sensor, or a moisture sensor, or the like. According to an embodiment, the acceleration sensor may sense the acceleration of the electronic device 100 and output the acceleration values of the electronic device 100 in three-axis (e.g., x, y, and z axes) directions. According to an embodiment, the gyro acceleration sensor may sense the angular velocity of the electronic device 100 to output the angular velocity values of the electronic device 100 in three-axis (e.g., x, y, and z axes) directions. According to an embodiment, the HRM sensor may measure the heart rate of the user. According to an embodiment, the moisture sensor may include a light emitting diode (LED) or a galvanic skin reflex (GSR) sensor.

According to an embodiment, the communication module 170 may include various communication circuitry and communicate with an external electronic device (e.g., a smartphone or a server). For example, the communication module 170 may receive information necessary to measure the body composition from the external electronic device or may transmit the result of measuring the body composition to the external electronic device. According to an embodiment, the communication module 170 may include various communication circuitry, such as, for example, and without limitation, a cellular module, a wireless-fidelity (Wi-Fi) module, a Bluetooth module, or a near field communication (NFC) module, or the like.

According to an embodiment, the processor 180 may include various processing circuitry and control overall operations of the electronic device 100. According to an embodiment, the processor 180 may control each of the transmission module 110, the reception module 120, the memory 130, the display 140, the input module 150, the sensor module 160, and the communication module 170 to measure the user's body composition according to various embodiments of the present disclosure. According to an embodiment, the electronic device 100 may include the at least one processor 180. For example, the electronic device 100 may include a plurality of processors 180 capable of executing at least one function. According to an embodiment, the processor 180 (e.g., an application processor) may be implemented with a system on chip (SoC) including, for example, and without limitation, a central processing unit (CPU), a graphic processing unit (GPU), a memory, or the like.

According to an embodiment, the processor 180 may store the profile information of the user in the memory 130. According to an embodiment, the processor 180 may store the profile information based on a user input received through the input module 150. For example, the processor 180 may store, in the memory 130, the user's height, age, weight, gender, or food intake history (e.g., a time, a type of food, or the like), which is received from the user or which is received from another electronic device through the communication module 170. According to an embodiment, the processor 180 may store the profile information based on information sensed through the sensor module 160. For example, the processor 180 may store the user's exercise history, sleep history, and stress index in the memory 130 based on the information obtained through the sensor module 160. According to an embodiment, the processor 180 may store the profile information received from the external electronic device, in the memory 130. According to an embodiment, the processor 180 may update the profile information stored in the memory 130.

According to an embodiment, the processor 180 may measure the user's body composition using at least one or more electrodes included in the electronic device 100. For example, if a user input to request body composition measurement is received through the input module 150, the processor 180 may measure the user's body composition. For another example, the processor 180 may measure the user's body composition at a preset time by the user or periodically.

According to an embodiment, the processor 180 may output a signal to the user's body through the transmission module 110 and may receive a signal, which passes through the user's body, through the reception module 120. According to an embodiment, the processor 180 may measure the user's body composition based on the received signal. For example, the characteristic (e.g., amplitude) of the signal that is transmitted from the transmission module 110 to the reception module 120 through the user's body may be changed by the user's body. The processor 180 may measure the user's body impedance based on the change in the signal received through the reception module 120. According to an embodiment, the processor 180 may measure the user's body composition based on the body impedance.

Figure 2A:
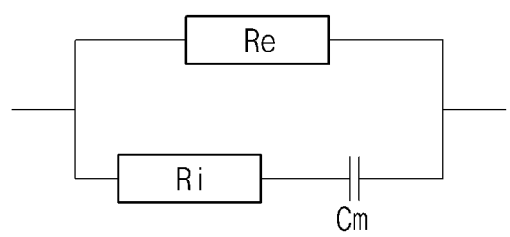
FIG. 2A is a diagram illustrating an example of a model of a user body.

FIG. 2A is a diagram illustrating an example of a model of a user body.

The body may be comprised of a plurality of cells and extracellular materials. The cell wall is comprised of a dual lipid membrane and may have a capacitance component, and a high-frequency current may be required to drive a current into a cell. As such, a low-frequency signal (e.g., 1 to 5 kHz) may flow through the extracellular material, and a high-frequency signal may flow through cells as well as extracellular materials. When the body is modeled depending on the above-mentioned body characteristics, the body may include an extracellular resistance component Re by extracellular water, an intracellular resistance component Ri by intracellular water, and a capacitance component Cm by the cell wall. The intracellular water may be the moisture that comprises the muscle, and the extracellular water may not be associated with muscle. It is necessary to distinguish the extracellular resistance component Re, the intracellular resistance component Ri, and the capacitance component Cm for the purpose of accurately measuring the body composition.

Figure 2B:
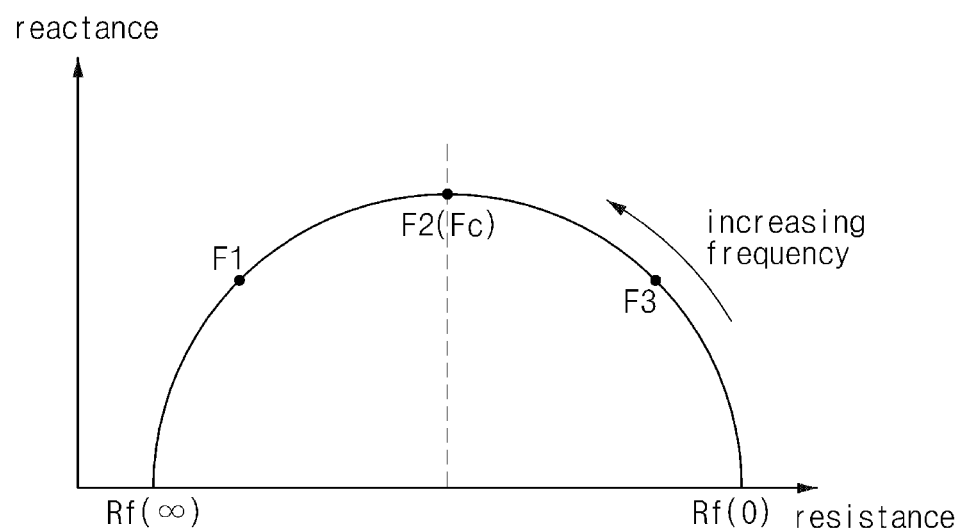
FIG. 2B is a diagram illustrating an example of body impedance based on a frequency.

FIG. 2B is a diagram illustrating an example of body impedance based on a frequency.

A graph illustrated in FIG. 2B may be obtained by measuring body impedance for each frequency with respect to the body model illustrated in FIG. 2A. Referring to FIG. 2B, if a current, the frequency of which is '0', is applied to a body, the current may not flow through the intracellular resistance component Ri due to the capacitance component Cm by cell wall, but the current may flow only through the extracellular resistance component Re. The body impedance Rf(0) measured when the frequency of the current is '0' may correspond to the extracellular resistance component Re. When a current, the frequency of which is infinity, is applied to the body, the current may flow through the extracellular resistance component Re and the intracellular resistance component Ri, and the capacitance component Cm by cell wall may be ignored. The body impedance Rf(∞) measured when the frequency of the current is infinity may correspond to the extracellular resistance component Re and the intracellular resistance component Ri. When the current, the frequency of which is between '0' and infinity (other than '0' and infinity) is applied to the body, the current may flow through the extracellular resistance component Re, the intracellular resistance component Ri, and the capacitance component Cm.

The body impedance based on the body model illustrated in FIG. 2A may be expressed by the following Equation 1.

$$Z = \left( \frac{1}{Re} + \frac{1}{\left(Ri + \frac{1}{i \cdot 2\pi \cdot f \cdot Cm}\right)} \right)^{-1} \quad \text{[Equation 1]}$$

In Equation 1, Z denotes the body impedance; Re denotes the extracellular resistance component; Ri denotes the intracellular resistance component; Cm denotes the capacitance component; and 'f' denotes the frequency of the signal.

According to an embodiment, the processor 180 may measure a user's body impedance using at least three signals having different frequencies. For example, referring to FIG. 2B, the processor 180 may measure the body impedance using three signals that respectively have a first frequency F1, a second frequency F2, and a third frequency F3. If three body impedances corresponding to three frequencies are measured, a semicircle passing through three body impedances may be obtained, and thus, the processor 180 may distinguish the extracellular resistance component Re, the intracellular resistance component Ri, and the capacitance component Cm.

According to an embodiment, as illustrated in FIG. 2B, the body impedance characteristic according to a frequency may appear in a semicircular form and may define a frequency, which has the greatest reactance value and which is placed at the center point of the semicircle, as a characteristic frequency Fc. In the case where the body impedance is measured using the characteristic frequency Fc, a frequency difference (a distance in a graph) between the characteristic frequency Fc and another frequency F1 or F3 may increase, and thus the accuracy may be improved.

According to an embodiment, considering the leakage current of capacitance component Cm, the body impedance based on the body model illustrated in FIG. 2A may be represented as the following Equation 2.

$$Z = \left( \frac{1}{Re} + \frac{1}{\left(Ri + \frac{1}{i \cdot 2\pi \cdot f \cdot Cm^{(1-\alpha)}}\right)} \right)^{-1} \quad \text{[Equation 2]}$$

In Equation 2, Z denotes the body impedance; Re denotes the extracellular resistance component; Ri denotes the intracellular resistance component; Cm denotes the capacitance component; a denotes a factor (or a parameter) by leakage current; and 'f' denotes the frequency of the signal. According to an embodiment, considering the influence of the leakage current in the capacitance component, the processor 180 may measure the body impedance using at least four signals having different frequencies.

According to an embodiment, the processor 180 may determine the frequency of at least one of at least three signals for measuring body composition, based on profile information stored in the memory 130. According to an embodiment, the processor 180 may determine at least one frequency including the characteristic frequency Fc, based on the profile information of a user. Even in the case of a person of the same weight, the body impedance of the person may be changed depending on a height, an age, a lifestyle, or the like, and the characteristic frequency Fc for measuring the user's body impedance may be also changed depending on a person. For example, as the user's weight increases, the characteristic frequency Fc may decrease. According to an embodiment, the processor 180 may determine at least one frequency including the characteristic frequency Fc corresponding to the profile information of the user, using the look-up table stored in the memory 130. According to an embodiment, other frequencies other than the characteristic frequency Fc may be set by default. According to an embodiment, if the body composition measuring result (or body composition information) is stored in the memory 130 when the measurement of the body composition is completed, the processor 180 may determine the characteristic frequency Fc based on the body composition information stored in the memory 130. When measuring the body composition of the user at first, the processor 180 fails to use the body composition information because the user's body composition information is not included in the profile information of the user. However, if measuring the body composition again, the processor 180 may determine the characteristic frequency using the body composition information. As such, when the body composition is measured again, it is possible to obtain the more accurate body composition analysis result compared with the initial measurement.

According to an embodiment, if frequencies of at least three signals are determined, the processor 180 may output a synthesis signal obtained by synthesizing at least three signals corresponding to the determined frequencies, through the transmission module 110. According to an embodiment, after removing a noise included in the synthesis signal using, for example, a filter, the processor 180 may output the synthesis signal.

According to an embodiment, the processor 180 may generate at least three signals corresponding to the determined frequency. According to an embodiment, the processor 180 may synthesize at least three signals to generate the synthesis signal. According to an embodiment, the processor 180 may output the generated synthesis signal through the transmission module 110. For example, after converting the synthesis signal generated by the processor 180 to an analog signal using a digital to analog converter (DAC), the transmission module 110 may output the analog signal.

According to another embodiment, the processor 180 may verify a synthesis signal, which corresponds to the determined frequency, from among a plurality of synthesis signals stored in the memory 130. According to an embodiment, the processor 180 may output the verified synthesis signal through the transmission module 110. For example, after converting the synthesis signal verified by the processor 180 to an analog signal using the DAC, the transmission module 110 may output the analog signal.

According to another embodiment, the processor 180 may output the sinc signal stored in the memory 130 through the transmission module 110. For example, the sinc signal may include a signal having a frequency that is different from the frequency determined based on the user's profile information. According to an embodiment, after converting the sinc signal stored in the memory 130 to an analog signal using the DAC, the transmission module 110 may output the analog signal.

According to another embodiment, the transmission module 110 may include at least three signal generators generating the analog signal and a signal synthesizer. According to an embodiment, the processor 180 may control the transmission module 110 to generate the synthesis signal. For example, the processor 180 may control the signal generators so as to generate at least three signals having the determined frequency. The signal synthesizer may synthesize at least three signals received from the signal generators to output the synthesis signal.

Figure 3A:
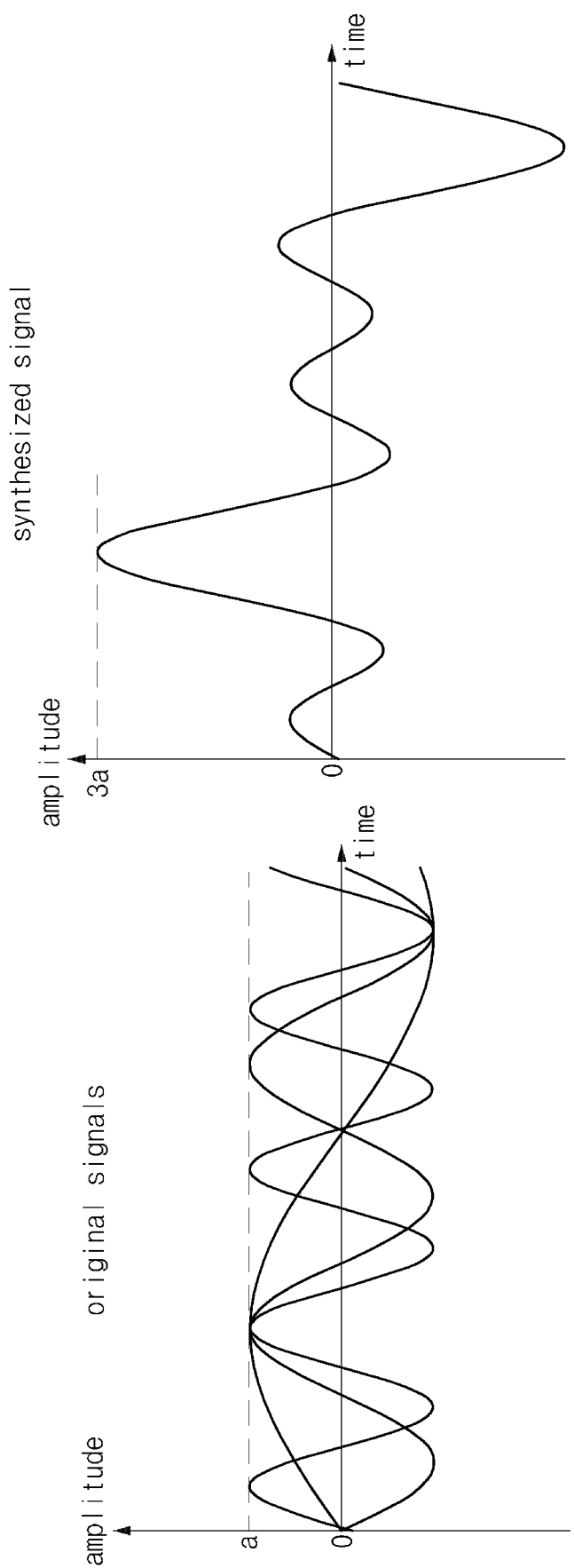
FIGS. 3A and 3B are diagrams illustrating an example synthesis signal, according to an example embodiment of the present disclosure.
Figure 3B:
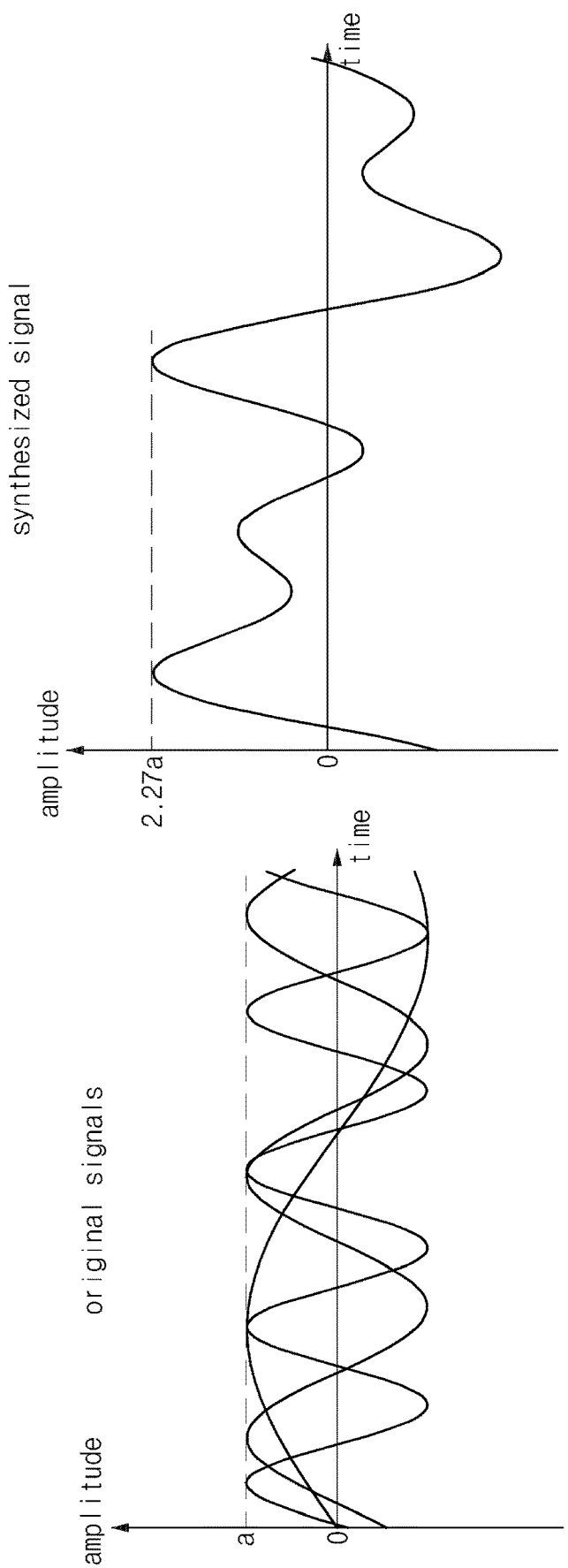

FIGS. 3A and 3B are graphs illustrating an example synthesis signal, according to an example embodiment of the present disclosure.

According to an embodiment, the processor 180 may adjust the phase of at least one among at least three signals such that the amplitude of a synthesis signal is minimized and/or reduced when synthesizing at least three signals.

Referring to FIG. 3A, in the case where three signals, which respectively have frequencies of 'f', '3f', and '5f' and the amplitude of which is 'a', is synthesized, the maximum amplitude of the synthesis signal may be 3a. Referring to FIG. 3B, in the case where the phase of at least part of the three signals having frequencies and amplitudes, which are the same as those of FIG. 3A, is adjusted and synthesized, the amplitude of the synthesis signal may be minimized to 2.27a.

In the case where a current is applied to a user's body to measure impedance, if the strength of the current exceeds a specified value, the user may feel the current flowing in his/her body, and thus the user may feel uncomfortable. For example, if the current intensity exceeds 400 µA in the case of male and if the current intensity exceeds 300 µA in the case of female, the male or female may feel the current flowing in his/her body. As the strength of a current increases, a measurement error may decrease. However, it is favorable that the strength of the current is set to less than maximum 300 µA, in consideration of the inconvenience of the user.

As illustrated in FIG. 3A, in the case where the maximum amplitude of the synthesis signal is 3a, the amplitude of each of the signals may be set to less than maximum 100 µA. However, as illustrated in FIG. 3B, in the case where the maximum amplitude of the synthesis signal is 2.27a, the amplitude of each of the signals may be set to less than maximum 137 µA. In the case where the phase of a signal is adjusted such that the amplitude of the synthesis signal is minimized, the strength of the current to be set to each of the signals may increase compared with the case where the phase of the signal is not adjusted. As such, it is possible to improve the accuracy of the body impedance measurement without giving a sense of discomfort to the user.

According to an embodiment, the processor 180 may measure the body impedance using the synthesis signal obtained by synthesizing at least three signals. For example, the processor 180 may output the synthesis signal to the user's body through the transmission module 110 and may receive the synthesis signal, which passes through the user's body, through the reception module 120.

Figure 4A:
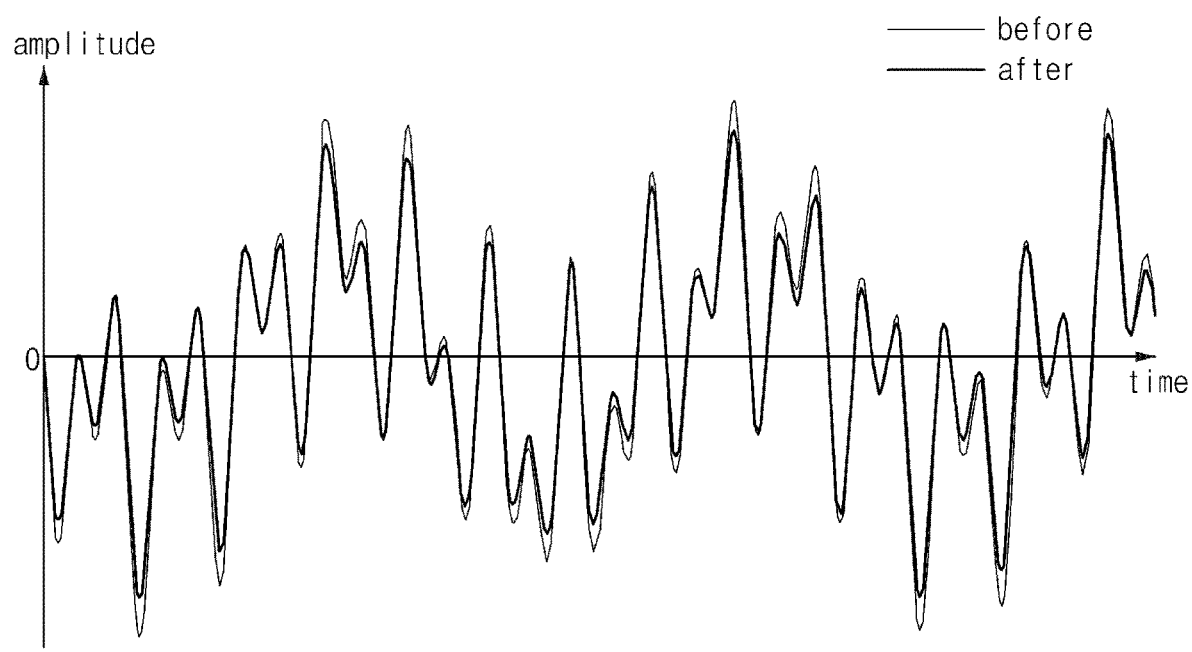
FIGS. 4A and 4B graphs illustrating an example change of a signal passing through a body, according to an example embodiment of the present disclosure.
Figure 4B:
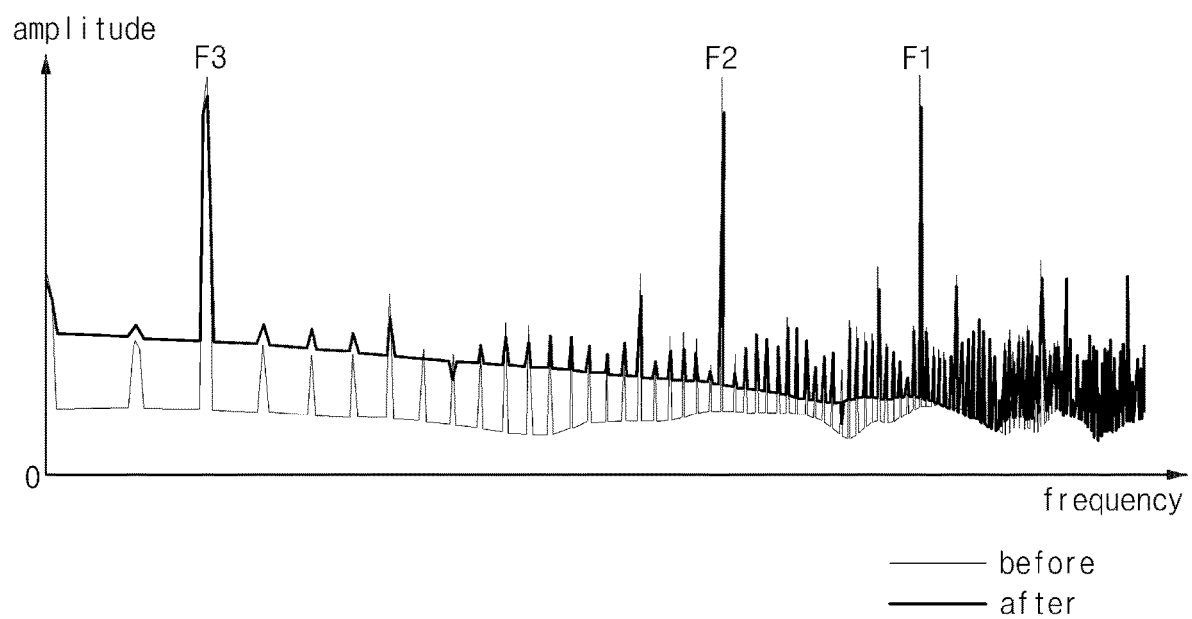

FIGS. 4A and 4B are graphs illustrating an example change of a signal passing through a body, according to an example embodiment of the present disclosure.

FIG. 4A is a graph illustrating the synthesis signal output by the transmission module 110 before passing through the body and a synthesis signal received by the reception module 120 after passing through the body in a time domain. Referring to FIG. 4A, if the synthesis signal passes through the body, it is understood that the amplitude is reduced by a resistance component included in the body.

FIG. 4B is a graph illustrating the synthesis signal output by the transmission module 110 before passing through the body and a synthesis signal received by the reception module 120 after passing through the body in a frequency domain. Referring to FIG. 4B, if the synthesis signal passes through the body, the magnitude of a signal may be reduced.

According to an embodiment, the processor 180 may verify signals respectively having frequencies before synthesis, based on the synthesis signal received through the reception module 120. For example, after converting the synthesis signal in the time domain to the synthesis signal in the frequency domain, the processor 180 may verify at least three signals respectively having frequencies before the synthesis. According to an embodiment, the processor 180 may compare an output signal with the received signal for each frequency to measure the body impedance for each frequency.

As the number of signals for measuring the body impedance increases, the accuracy of body composition measurement may be improved. However, a time required to measure body composition may increase. According to various embodiments of the present disclosure, the processor 180 may measure the body impedance using the synthesis signal obtained by synthesizing signals of a plurality of frequencies, thereby maintaining the accuracy of the body composition measurement and reducing a time required to measure the body composition.

Figure 5A:
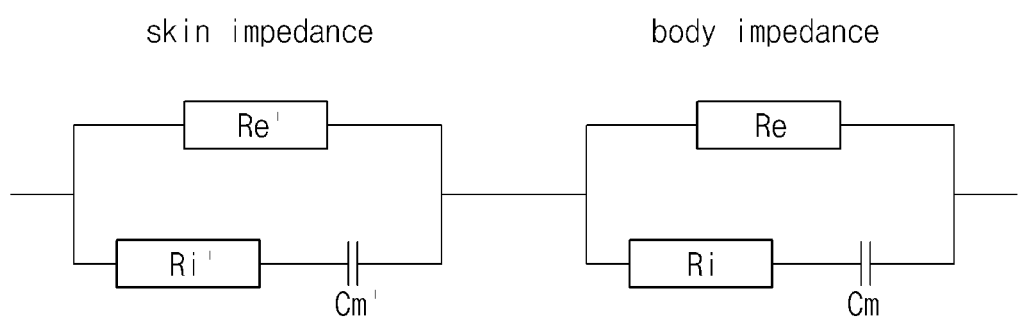
FIG. 5A is a diagram illustrating another example of a model of a user body.

FIG. 5A is a diagram illustrating another example of a model of a user body.

The surface of the body may be covered with skin, and the skin may have electrical characteristics different from those of the inside of the body. In the case where the user contacts the electronic device 100 to measure body composition, the impedance due to contact between the skin and an electrode may be considered. In the case where the contact area between the skin and the electrode is wide (e.g., 100 to 300 cm$^2$), the contact impedance may be negligible because the contact impedance has a value much smaller than the body impedance. In the case where the contact area between the skin and the electrode is narrow (e.g., 0.3 to 0.6 cm$^2$), the influence due to the skin contact impedance may increase. In a small device such as a wearable device, the contact area between the skin and the electrode may be narrowed because the size of the electrode is restricted, and thus it is necessary to consider the influence due to the skin contact impedance. If the user's body is modeled in consideration of the skin contact impedance, the impedance of the body may include body component Re, Ri, or Cm and skin component Re', Ri', or Cm', and the body component and the skin component may be serially connected to each other.

Figure 5B:
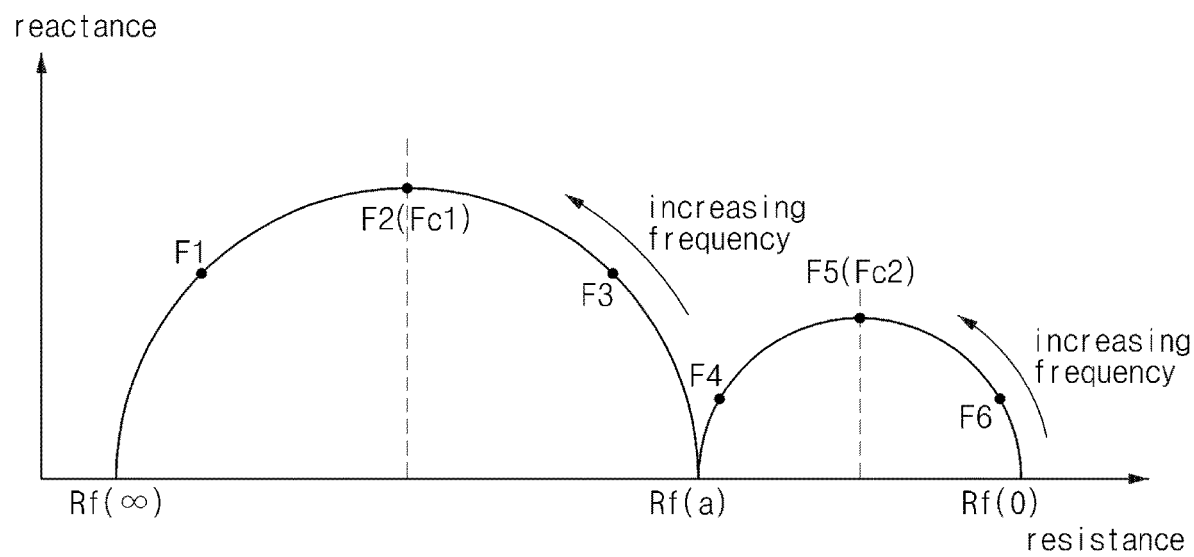
FIG. 5B is a diagram illustrating another example of body impedance based on a frequency.

FIG. 5B is a diagram illustrating another example of body impedance based on a frequency.

A graph illustrated in FIG. 5B may be obtained by measuring body impedance for each frequency with respect to the body model illustrated in FIG. 5A. The skin contact impedance may be ignored in a first frequency range where the change of the skin contact impedance is small, and the influence by the body may be ignored in a second frequency range where the change of the body impedance is small. The second frequency range may be smaller than the first frequency range. For example, the first frequency range and the second frequency range may be distinguished by frequency 'a' (e.g., 10 KHz).

In a frequency (or a frequency of 10 KHz to 1 MHz (or 2 MHz)) of 'a' to infinity that is the first frequency range, only the body impedance may be considered. If a current, the frequency of which is 'a', is applied to a body, the current may not flow through the intracellular resistance component Ri due to the capacitance component Cm by cell wall, but the current may flow only through the extracellular resistance component Re. The body impedance Rf(a) measured when the frequency of the current is 'a' may correspond to the extracellular resistance component Re. When a current, the frequency of which is infinity, is applied to the body, the current may flow through the extracellular resistance component Re and the intracellular resistance component Ri, and the capacitance component Cm by cell wall may be ignored. The body impedance Rf(∞) measured when the frequency of the current is infinity may correspond to the extracellular resistance component Re and the intracellular resistance component Ri. When the current, the frequency of which is between 'a' and infinity (other than 'a' and infinity) is applied to the body, the current may flow through the extracellular resistance component Re, the intracellular resistance component Ri, and the capacitance component Cm.

In a frequency (or a frequency of 1 KHz to 10 KHz) of '0' to 'a' that is the second frequency range, only the skin contact impedance may be considered. If a current, the frequency of which is '0', is applied to a body, the current may not flow through the skin intracellular resistance component Ri' due to the capacitance component Cm' by skin cell wall, but the current may flow only through the skin extracellular resistance component Re'. The skin contact impedance Rf(0) measured when the frequency of the current is '0' may correspond to the skin extracellular resistance component Re'. When a current, the frequency of which is 'a', is applied to the body, the current may flow through the skin extracellular resistance component Re' and the skin intracellular resistance component Ri', and the capacitance component Cm' by skin cell wall may be ignored. The skin contact impedance Rf(a) measured when the frequency of the current is 'a' may correspond to the skin extracellular resistance component Re' and the skin intracellular resistance component Ri'. When the current, the frequency of which is between '0' and 'a' (other than '0' and 'a') is applied to the body, the current may flow through the skin extracellular resistance component Re', the skin intracellular resistance component Ri', and the skin capacitance component Cm'.

The body impedance based on the body model illustrated in FIG. 5A may be expressed by the following Equation 3.

$$Z = \left( \frac{1}{Re'} + \frac{1}{\left( Ri' + \frac{1}{i \cdot 2\pi \cdot f \cdot Cm'} \right)} \right)^{-1} + \left( \frac{1}{Re} + \frac{1}{\left( Ri + \frac{1}{i \cdot 2\pi \cdot f \cdot Cm} \right)} \right)^{-1}$$ [Equation 3]

In Equation 3, Z denotes the body impedance; Re' denotes the skin extracellular resistance component; Ri' denotes the skin intracellular resistance component; Cm' denotes the capacitance component by the skin cell wall; Re denotes the body extracellular resistance component; Ri denotes the body intracellular resistance component; Cm denotes the capacitance component by the body cell wall; and 'f' denotes the frequency of a signal.

According to an embodiment, the processor 180 may measure a user's skin contact impedance based on a synthesis signal and may remove the skin contact impedance from the body impedance. According to an embodiment, the processor 180 may measure a user's body impedance using at least six signals having different frequencies, in consideration of the skin contact impedance. For example, referring to FIG. 5B, the processor 180 may measure the body impedance using six signals having a first frequency F1, a second frequency F2, and a third frequency F3, which are included in the first frequency range (e.g., 10 kHZ to 1 MHZ), and a fourth frequency F4, a fifth frequency F5, and a sixth frequency F6, which are included in the second frequency range (e.g., 1 Hz to 10 kHZ). If six body impedances corresponding to the six frequencies are measured, the processor 180 may obtain two semicircles passing through the six body impedances and may measure the skin contact impedance using at least three signals included in the second frequency range. As such, the processor 180 may distinguish the skin extracellular resistance component Re', the skin intracellular resistance component Ri', the capacitance component Cm' by the skin cell wall, the body extracellular resistance component Re, the body intracellular resistance component Ri, and the capacitance component Cm by cell wall.

According to an embodiment, as illustrated in FIG. 5B, the body impedance characteristic according to the frequency may appear in the form of two semicircles. A frequency, which has the greatest reactance value in the first frequency domain (e.g., 'a' to infinity) and which is placed at the center point of the semicircle, may be defined as a first characteristic frequency Fc1. A frequency, which has the greatest reactance value in the second frequency domain (e.g., '0' to 'a') and which is placed at the center point of the semicircle, may be defined as a second characteristic frequency Fc2. In the case where the body impedance is measured using the first characteristic frequency Fc1 and the second characteristic frequency Fc2, a frequency difference (the distance in a graph) from other frequencies (F1 and F3 or F4 and F6) may increase, and thus the accuracy may be improved.

According to an embodiment, considering the leakage current of capacitance component Cm or Cm', the body impedance based on the body model illustrated in FIG. 5A may be represented as the following Equation 4.

$$Z = \left( \frac{1}{Re'} + \frac{1}{\left( Ri' + \frac{1}{i \cdot 2\pi \cdot f \cdot Cm'^{(1-\alpha')}} \right)} \right)^{-1} + \left( \frac{1}{Re} + \frac{1}{\left( Ri + \frac{1}{i \cdot 2\pi \cdot f \cdot Cm^{(1-\alpha)}} \right)} \right)^{-1}$$ [Equation 4]

In Equation 4, Z denotes the body impedance; Re' denotes the skin extracellular resistance component; Ri' denotes the skin intracellular resistance component; Cm' denotes the capacitance component by the skin cell wall; $\alpha'$ denotes a factor (or a parameter) by a leakage current of the capacitance component by the skin cell wall; Re denotes the body extracellular resistance component; Ri denotes the body intracellular resistance component; Cm denotes the capacitance component by the body cell wall; a denotes a factor (or a parameter) by a leakage current of the capacitance component by the body cell wall; and 'f' denotes the frequency of the signal. According to an embodiment, considering the influence of the leakage current that is present in the capacitance component, the processor 180 may measure the body impedance using at least eight signals having different frequencies.

According to an embodiment, the processor 180 may measure the user's body composition based on the body impedance for each frequency. For example, the processor 180 may verify the extracellular resistance component Re, the intracellular resistance component Ri, and the capacitance component Cm of the body, depending on the body composition measuring result for each frequency. The processor 180 may measure the user's body composition based on the magnitude, ratio, or the like of each component.

According to an embodiment, if the body composition measurement is completed, the processor 180 may store the body composition measuring result (or body composition information) as user profile information in the memory 130. According to an embodiment, the body composition information stored in the memory 130 may be used to determine the frequency of a signal for measuring the body composition in a process of measuring the body composition, which is going to be performed afterwards.

Figure 6A:
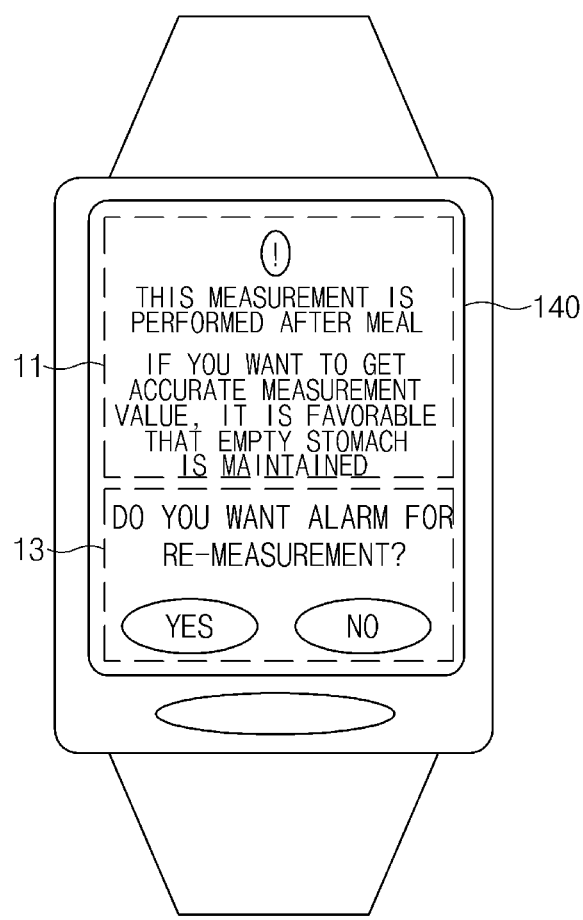
FIGS. 6A and 6B are diagrams illustrating an example user interface displayed in a display, according to an example embodiment of the present disclosure.
Figure 6B:
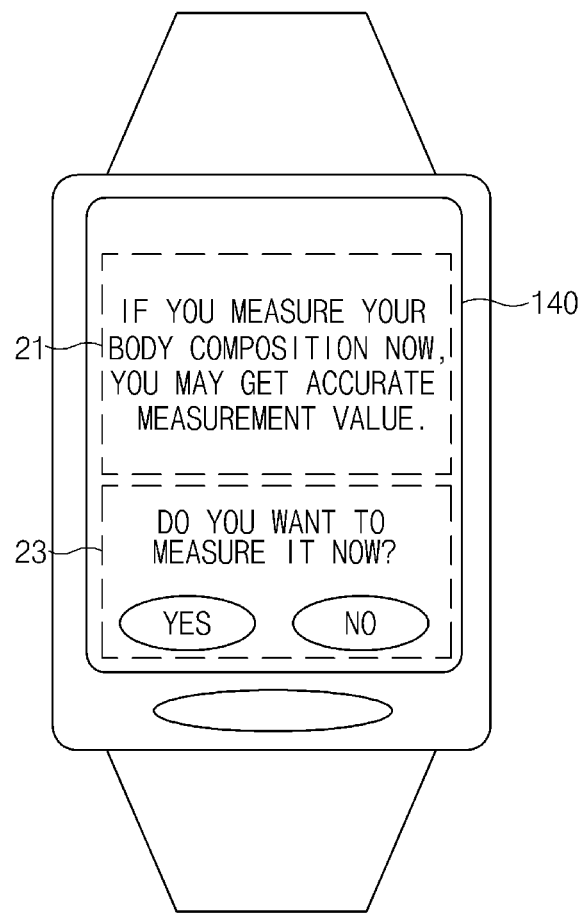

FIGS. 6A and 6B are diagrams illustrating an example user interface displayed in a display of an electronic device, according to an example embodiment of the present disclosure.

According to an embodiment, the processor 180 may verify a user's body state based on profile information that is before or after measuring the body fat. For example, the processor 180 may verify a user's recent exercise time, wake-up time, recent food intake time, or the like. According to an embodiment, the processor 180 may determine whether the user's body state satisfies a specified standard. For example, the processor 180 may determine whether a specified time elapses after exercise, whether a specified time elapses after food intake, whether a specified time elapses after wake-up, whether to correspond to the menstrual cycle, or the like. According to an embodiment, if the user's state does not satisfy a specified standard, the processor 180 may display a user interface for providing notification that an error may be included in the measured body composition, in the display 140. For example, referring to FIG. 6A, if a specified time does not elapse after food intake, the processor 180 may display a user interface 11 for providing notification that an error may be included in the measured body composition due to the measurement after a meal, in the display 140. The processor 180 may display a user interface 13 capable of setting an alarm for measuring the body composition. If an alarm for measuring the body composition is set, when a set time elapses or when the state of the user is changed to satisfy a specified standard, the processor 180 may provide the alarm for measuring the body composition.

According to an embodiment, if the state of the user satisfies the specified standard, the processor 180 may display a user interface for providing notification that the state of the user is a state suitable to measure the body composition, in the display 140. For example, referring to FIG. 6B, if the state of the user is changed to satisfy a specified standard, or if a set alarm time elapses, the processor 180 may display a user interface 21 for providing notification that the state of the user is a state suitable to measure the body composition, in the display 140. The processor 180 may display a user interface 23 capable of measuring the body composition together.

Figure 7:
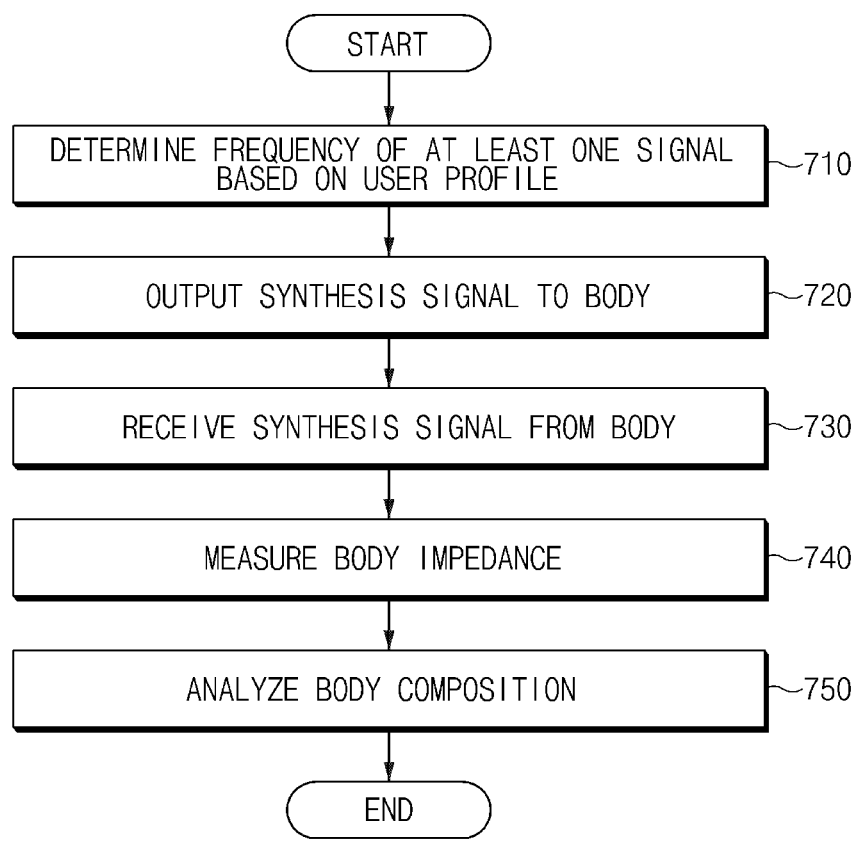
FIG. 7 is a flowchart illustrating an example body composition measuring method of an electronic device, according to an example embodiment of the present disclosure.

FIG. 7 is a flowchart illustrating an example body composition measuring method of an electronic device, according to an example embodiment of the present disclosure.

The flowchart illustrated in FIG. 7 may include operations processed by the above-described electronic device 100. Therefore, although there are contents omitted below, details that are described about the electronic device 100 with reference to FIGS. 1 to 6B may be applied to the flowchart illustrated in FIG. 7.

According to an embodiment, in operation 710, the electronic device 100 may determine the frequency of at least one of at least three signals for measuring body composition, based on profile information of a user. For example, the processor 180 may determine at least one frequency including the characteristic frequency Fc corresponding to the profile information of the user, using the look-up table stored in the memory 130.

According to an embodiment, in operation 720, the processor 180 included in the electronic device 100 may output a synthesis signal to the user's body using at least one first electrode included in the transmission module 110. For example, in a state where the transmission module 110 contacts the user's body, the processor 180 may output the synthesis signal to the user's body using the transmission module 110. For example, the synthesis signal may include a signal corresponding to the determined frequency in operation 710.

According to an embodiment, after generating at least three signals corresponding to the determined frequency, the processor 180 included in the electronic device 100 may synthesize the generated signals. The processor 180 may adjust the phase of at least one among at least three signals such that the amplitude of a synthesis signal is minimized and/or reduced when synthesizing the signals. According to another embodiment, the processor 180 may output a synthesis signal, which corresponds to the determined frequency, from among a plurality of synthesis signals stored in a memory through the transmission module 110. According to another embodiment, the processor 180 may output a sinc signal including a signal, which is stored in the memory and which corresponds to the determined frequency, through the transmission module 110.

According to an embodiment, in operation 730, the processor 180 included in the electronic device 100 may receive a synthesis signal from the user's body using at least one second electrode included in the reception module 120. For example, in a state where the reception module 120 contacts the user's body, the processor 180 may receive the synthesis signal passing through the user's body, using the reception module 120. If the synthesis signal passes through the body, the amplitude may be reduced by the resistance component included in the body.

According to an embodiment, in operation 740, the processor 180 included in the electronic device 100 may measure the user's body impedance based on the received synthesis signal. For example, after converting the synthesis signal in the time domain to the synthesis signal in the frequency domain, the processor 180 may verify at least three signals respectively having frequencies before the synthesis. The processor 180 may compare an output signal with the received signal for each frequency to measure the body impedance for each frequency.

According to an embodiment, in operation 750, the processor 180 included in the electronic device 100 may analyze the user's body composition based on the user's body impedance. For example, the processor 180 may verify the extracellular resistance component Re, the intracellular resistance component Ri, and the capacitance component Cm of the body, depending on the body composition measuring result for each frequency. The processor 180 may measure the user's body composition based on the magnitude, ratio, or the like of each component.

According to an embodiment, the processor 180 included in the electronic device 100 may verify the user's state based on profile information that is before or after measuring the body fat. According to an embodiment, the processor 180 may determine whether the user's body state satisfies a specified standard. According to an embodiment, if the user's state does not satisfy a specified standard, the processor 180 may display a user interface for providing notification that an error may be included in the measured body composition, through the display 140. According to an embodiment, if the state of the user is changed to satisfy the specified standard, the processor 180 may display a user interface for providing notification that the state of the user is a state suitable to measure the body composition, through the display 140.

According to another embodiment, the processor 180 included in the electronic device 100 may receive the synthesis signal output through the transmission module 110, using the reception module 120. The received synthesis signal may be a signal that passes through the user's body contacting the electronic device 100. The processor 180 may transmit at least one information associated with the received synthesis signal, to any other electronic device (e.g., a smartphone, a tablet, a server, or the like) using the communication module 170. The other electronic device may obtain (calculate) a value associated with the user's body composition, based on the information received from the electronic device 100. The processor 180 may receive a value associated with the user's body composition, from the other electronic device through the communication module 170 and may display the received value through the display 140.

Figure 8:
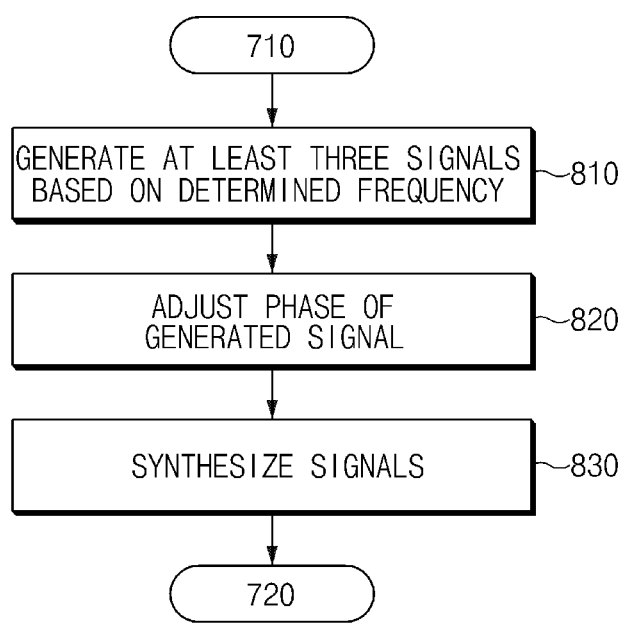
FIG. 8 is a flowchart illustrating an example signal synthesizing method of an electronic device, according to an example embodiment of the present disclosure.

FIG. 8 is a flowchart illustrating an example signal synthesizing method of an electronic device, according to an example embodiment of the present disclosure.

The flowchart illustrated in FIG. 8 may include operations processed by the above-described electronic device 100 and may be performed after operation 710 of FIG. 7. Therefore, although there are contents omitted below, details that are described about the electronic device 100 with reference to FIGS. 1 to 6B may be applied to the flowchart illustrated in FIG. 8.

According to an embodiment, in operation 810, the processor 180 included in the electronic device 100 may generate at least three signals based on the determined frequency. For example, the processor 180 may generate at least three signals of a digital waveform using a software module or may generate at least three signals of an analog waveform using at least three signal generators included in a transmission module.

According to an embodiment, in operation 820, the processor 180 may adjust the phase of at least one among at least three signals such that the amplitude of a synthesis signal is minimized and/or reduced.

According to an embodiment, in operation 830, the processor 180 may synthesize at least three signals. For example, the processor 180 may synthesize at least three signals of a digital waveform using the software module or may synthesize at least three signals of an analog waveform using at least synthesizer included in the transmission module.

Figure 9:
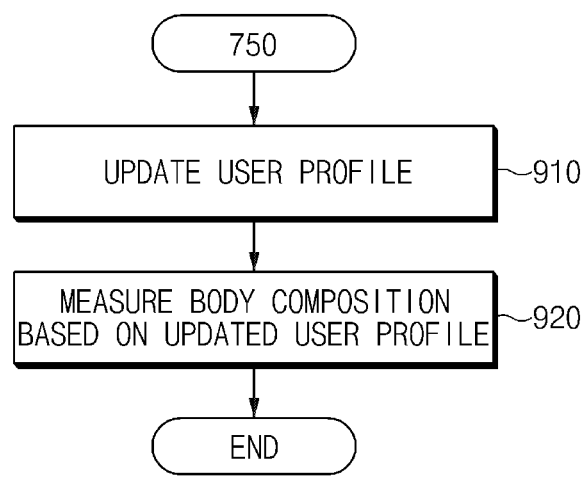
FIG. 9 is a flowchart illustrating an example body composition measuring method of an electronic device, according to an example embodiment of the present disclosure.

FIG. 9 is a flowchart illustrating an example body composition measuring method of an electronic device, according to an example embodiment of the present disclosure.

The flowchart illustrated in FIG. 9 may include operations processed by the above-described electronic device 100 and may be performed after operation 750 of FIG. 7. Therefore, although there are contents omitted below, details that are described about the electronic device 100 with reference to FIGS. 1 to 6B may be applied to the flowchart illustrated in FIG. 9.

According to an embodiment, if the body composition measurement is completed, in operation 910, the processor 180 included in the electronic device 100 may update a user profile. For example, the processor 180 may store the body composition analyzing result (or body composition information) as user profile information in a memory. For another example, if the body composition information stored in the memory is present, the processor 180 may update the body composition information based on the body composition analyzing result.

According to an embodiment, in operation 920, the processor 180 may measure the body composition based on the updated user profile. The processor 180 may measure the body composition based on the updated user profile depending on the body composition measuring method described with reference to FIG. 7. For example, the processor 180 may determine the frequency of at least one among at least three signals for measuring the body composition, based on the body composition information included in the updated profile information and may measure the user's body composition using the synthesis signal generated depending on the determined frequency.

Figure 10:
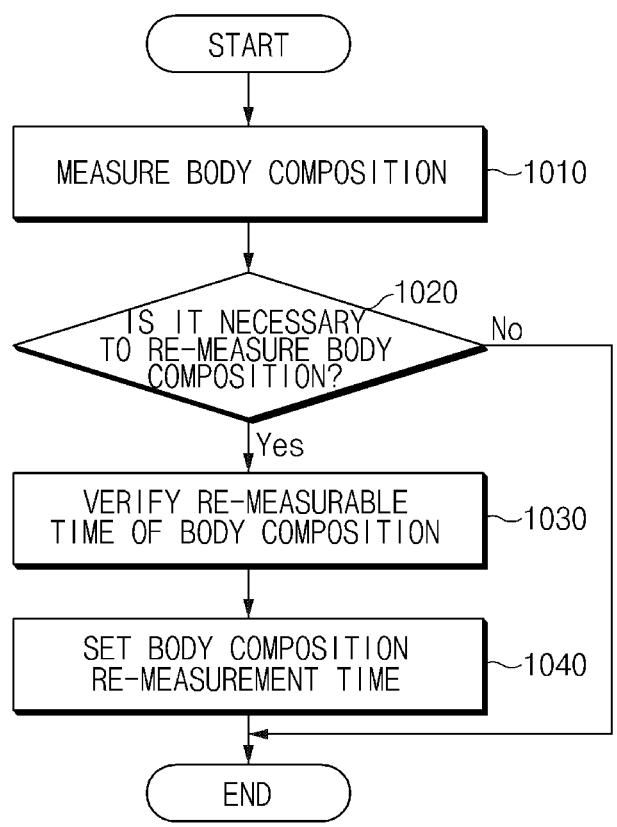
FIG. 10 is a flowchart illustrating an example body composition measuring method of an electronic device, according to an example embodiment of the present disclosure.

FIG. 10 is a flowchart illustrating an example body composition measuring method of an electronic device, according to an example embodiment of the present disclosure.

The flowchart illustrated in FIG. 10 may include operations processed by the above-described electronic device 100. Therefore, although there are contents omitted below, details that are described about the electronic device 100 with reference to FIGS. 1 to 6B may be applied to the flowchart illustrated in FIG. 10.

According to an embodiment, in operation 1010, the processor 180 included in the electronic device 100 may measure body composition of a user. For example, the processor 180 may measure the body composition depending on the body composition measuring method described with reference to FIG. 7.

According to an embodiment, in operation 1020, the processor 180 may determine whether it is necessary to re-measure the body composition. The processor 180 may verify the user's body state based on the profile information and may determine whether the state of the user satisfies a specified standard. If the state of the user does not satisfy a specified standard, the electronic device 100 may determine whether it is necessary to re-measure the body composition.

According to an embodiment, if it is determined that it is necessary to re-measure the body composition, in operation 1030, the processor 180 may verify a re-measurable time. For example, the processor 180 may verify a time when a state where the user's body state satisfies a specified standard elapses, based on the profile information.

According to an embodiment, in operation 1040, the processor 180 may set a body composition re-measurement time. For example, if it is determined that it is necessary to re-measure the body composition, the processor 180 may display a user interface capable of setting an alarm for re-measuring the body composition, through the display 140 and may set the re-measurement time depending on a user input received through a user interface.

Figure 11:
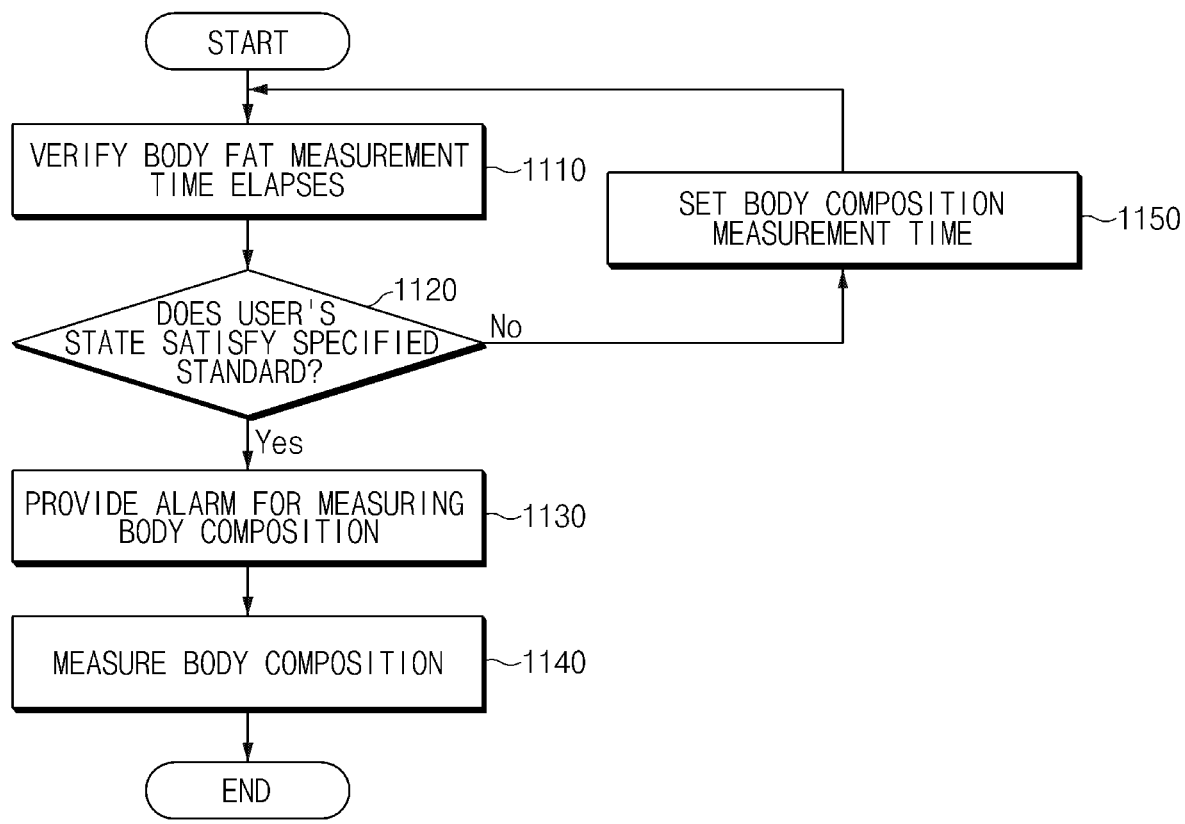
FIG. 11 is a flowchart illustrating an example body composition measuring method of an electronic device, according to an example embodiment of the present disclosure.

FIG. 11 is a flowchart illustrating an example body composition measuring method of an electronic device, according to an example embodiment of the present disclosure.

The flowchart illustrated in FIG. 11 may include operations processed by the above-described electronic device 100. Therefore, although there are contents omitted below, details that are described about the electronic device 100 with reference to FIGS. 1 to 6B may be applied to the flowchart illustrated in FIG. 11.

According to an embodiment, in operation 1110, the processor 180 included in the electronic device 100 may verify that a body fat measurement time elapses. For example, the processor 180 may verify that a time set by the user (e.g., 8 AM daily) has arrived. For another example, since the user's body state does not satisfy a specified standard, the processor 180 may verify that a time set to re-measure body fat has arrived.

According to an embodiment, in operation 1120, the processor 180 may determine whether the user's state satisfies the specified standard. For example, the processor 180 may determine whether a specified time elapses after exercise, whether a specified time elapses after food intake, whether a specified time elapses after wake-up, whether to correspond to the menstrual cycle, or the like, based on profile information of the user.

According to an embodiment, if the user's state satisfies the specified standard, in operation 1130, the processor 180 may provide an alarm for measuring body composition. For example, the electronic device 100 may display a user interface for providing notification that the state of the user is a state suitable to measure the body composition, through the display 140 and may output audio or may vibrate.

According to an embodiment, in operation 1140, the processor 180 may measure the user's body composition. For example, the processor 180 may measure the body composition depending on the body composition measuring method described with reference to FIG. 7.

According to an embodiment, if the user's state in operation 1120 does not satisfy the specified standard, in operation 1150, the processor 180 may set the body composition measurement time. For example, the processor 180 may display a user interface capable of setting an alarm for measuring the body composition, through the display 140 and may set the body composition measurement time depending on the user input received through the user interface.

Figure 12:
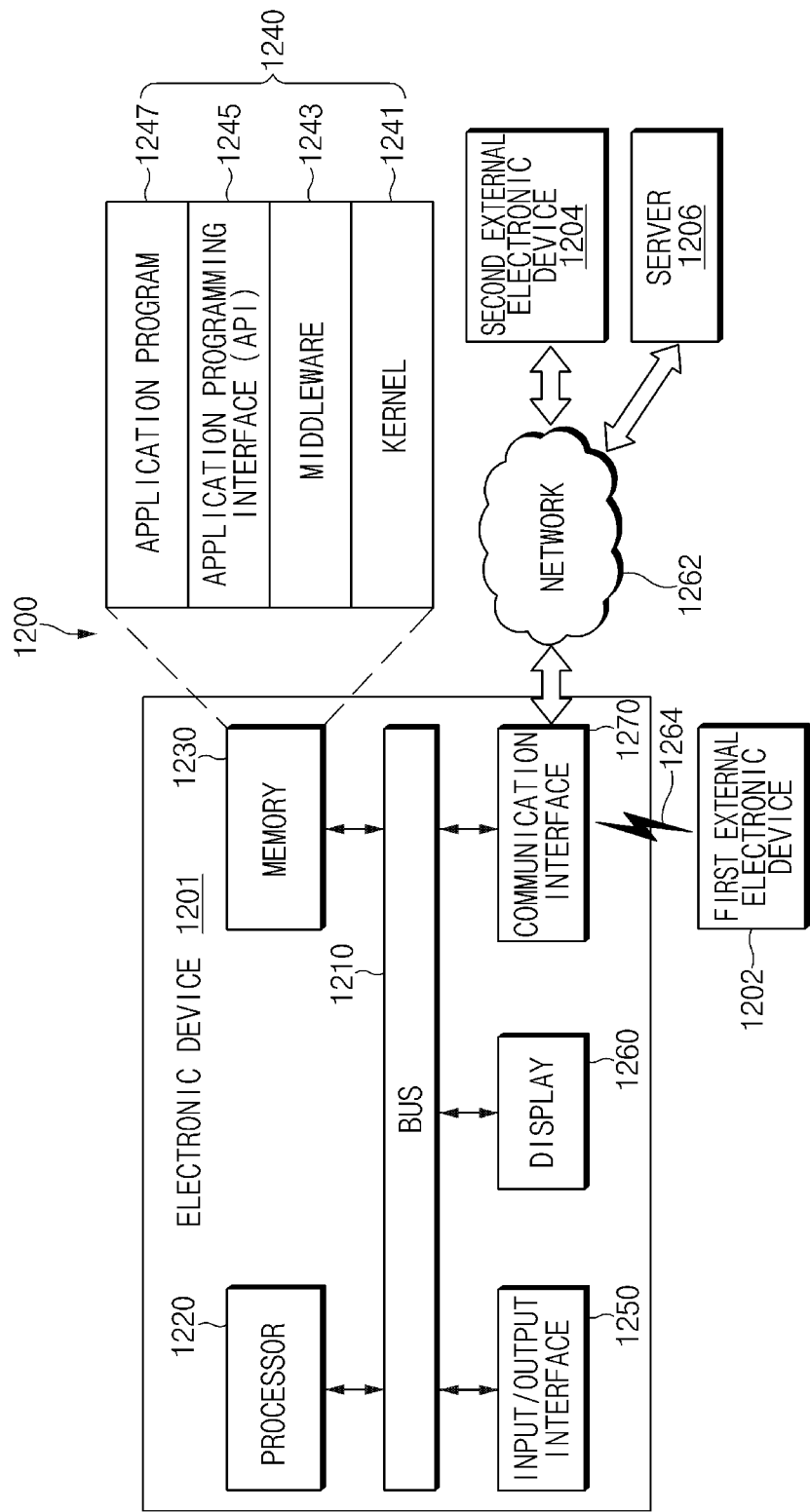
FIG. 12 is a diagram illustrating an example electronic device in a network environment, according to various example embodiments of the present disclosure.

FIG. 12 is a diagram illustrating an example electronic device in a network environment, according to various example embodiments of the present disclosure.

Referring to FIG. 12, there is illustrated an electronic device 1201 in a network environment 1200 according to various embodiments. The electronic device 1201 may include a bus 1210, a processor 1220, a memory 1230, an input/output (I/O) interface 1250, a display 1260, and a communication interface 1270. According to an embodiment, the electronic device 1201 may not include at least one of the above-described elements or may further include other element(s).

The bus 1210 may interconnect the above-described elements 1210 to 1270 and may include a circuit for conveying communications (e.g., a control message or data) among the above-described elements.

The processor 1220 may include various processing circuitry, such as, for example, and without limitation, one or more of a dedicated processor, a central processing unit (CPU), an application processor (AP), or a communication processor (CP), or the like. The processor 1220 may perform, for example, data processing or an operation associated with control or communication of at least one other element(s) of the electronic device 1201.

The memory 1230 may include a volatile and/or nonvolatile memory. For example, the memory 1230 may store instructions or data associated with at least one other element(s) of the electronic device 1201. According to an embodiment, the memory 1230 may store software and/or a program 1240. The program 1240 may include, for example, a kernel 1241, a middleware 1243, an application programming interface (API) 1245, and/or an application program (or an "application") 1247.

At least a part of the kernel 1241, the middleware 1243, or the API 1245 may be called an "operating system (OS)". The kernel 1241 may control or manage system resources (e.g., the bus 1210, the processor 1220, the memory 1230, and the like) that are used to execute operations or functions of other programs (e.g., the middleware 1243, the API 1245, and the application program 1247). Furthermore, the kernel 1241 may provide an interface that allows the middleware 1243, the API 1245, or the application program 1247 to access discrete components of the electronic device 1201 so as to control or manage system resources.

The middleware 1243 may perform, for example, a mediation role such that the API 1245 or the application program 1247 communicates with the kernel 1241 to exchange data. Furthermore, the middleware 1243 may process one or more task requests received from the application program 1247 according to a priority. For example, the middleware 1243 may assign the priority, which makes it possible to use a system resource (e.g., the bus 1210, the processor 1220, the memory 1230, or the like) of the electronic device 1201, to at least one of the application program 1247 and may process the task requests.

The API 1245 may be an interface through which the application program 1247 controls a function provided by the kernel 1241 or the middleware 1243, and may include, for example, at least one interface or function (e.g., an instruction) for a file control, a window control, image processing, a character control, or the like. For example, the I/O interface 1250 may transmit an instruction or data, input from a user or another external device, to other element(s) of the electronic device 1201, or may output an instruction or data, input from the other element(s) of the electronic device 1201, to the user or the external device.

The display 1260 may include, for example, a liquid crystal display (LCD), a light-emitting diode (LED) display, an organic LED (OLED) display, or a microelectromechanical systems (MEMS) display, or an electronic paper display, or the like, but is not limited thereto. The display 1260 may display, for example, various kinds of contents (e.g., a text, an image, a video, an icon, a symbol, or the like) to a user. The display 1260 may include a touch screen and may receive, for example, a touch, gesture, proximity, or hovering input using an electronic pen or a portion of a user's body.

The communication interface 1270 may establish communication between the electronic device 1201 and an external electronic device (e.g., a first external electronic device 1202, a second external electronic device 1204, or a server 1206). For example, the communication interface 1270 may be connected to a network 1262 through wireless communication or wired communication to communicate with an external device (e.g., the second external electronic device 1204 or the server 1206). The communication interface 1270 may also establish short-range wireless communication 1264 with an external electronic device, e.g., first external electronic device 1202.

The wireless communication may include a cellular communication that uses at least one of, for example, a long-term evolution (LTE), an LTE Advance (LTE-A), a code division multiple access (CDMA), a wideband CDMA (WCDMA), a universal mobile telecommunications system (UMTS), a wireless broadband (WiBro), a global system for mobile communications (GSM), or the like. According to an embodiment, the local area network may include at least one of wireless fidelity (Wi-Fi), Bluetooth, Bluetooth low energy (BLE), Zigbee, near field communication (NFC), magnetic secure transmission (MST), or radio frequency (RF), or body area network (BAN). According to an embodiment, a wireless communication may include the GNSS. The GNSS may be, for example, a global positioning system (GPS), a global navigation satellite system (Glonass), a Beidou Navigation Satellite System (hereinafter referred to as "Beidou"), or an European global satellite-based navigation system (Galileo). In this specification, "GPS" and "GNSS" may be interchangeably used. The wired communication may include at least one of, for example, a universal serial bus (USB), a high definition multimedia interface (HDMI), a recommended standard-232 (RS-232), a power line communication, a plain old telephone service (POTS), or the like. The network 1262 may include at least one of a telecommunication network, for example, a computer network (e.g., LAN or WAN), an Internet, or a telephone network.

Each of the first and second external electronic devices 1202 and 1204 may be a device of which the type is different from or the same as that of the electronic device 1201. According to various embodiments, all or a part of operations that the electronic device 1201 will perform may be executed by another or plural electronic devices (e.g., the first external electronic device 1202, the second external electronic device 1204, or the server 1206). According to an embodiment, in the case where the electronic device 1201 executes any function or service automatically or in response to a request, the electronic device 1201 may not perform the function or the service internally, but, alternatively additionally, it may request at least a portion of a function associated with the electronic device 101 from other device (e.g., the first external electronic device 1202, the second external electronic device 1204, or the server 1206). The other electronic device (e.g., the first external electronic device 1202, the second external electronic device 1204 or the server 1206) may execute the requested function or additional function and may transmit the execution result to the electronic device 1201. The electronic device 1201 may provide the requested function or service by processing the received result as it is, or additionally. To this end, for example, cloud computing, distributed computing, or client-server computing may be used.

Figure 13:
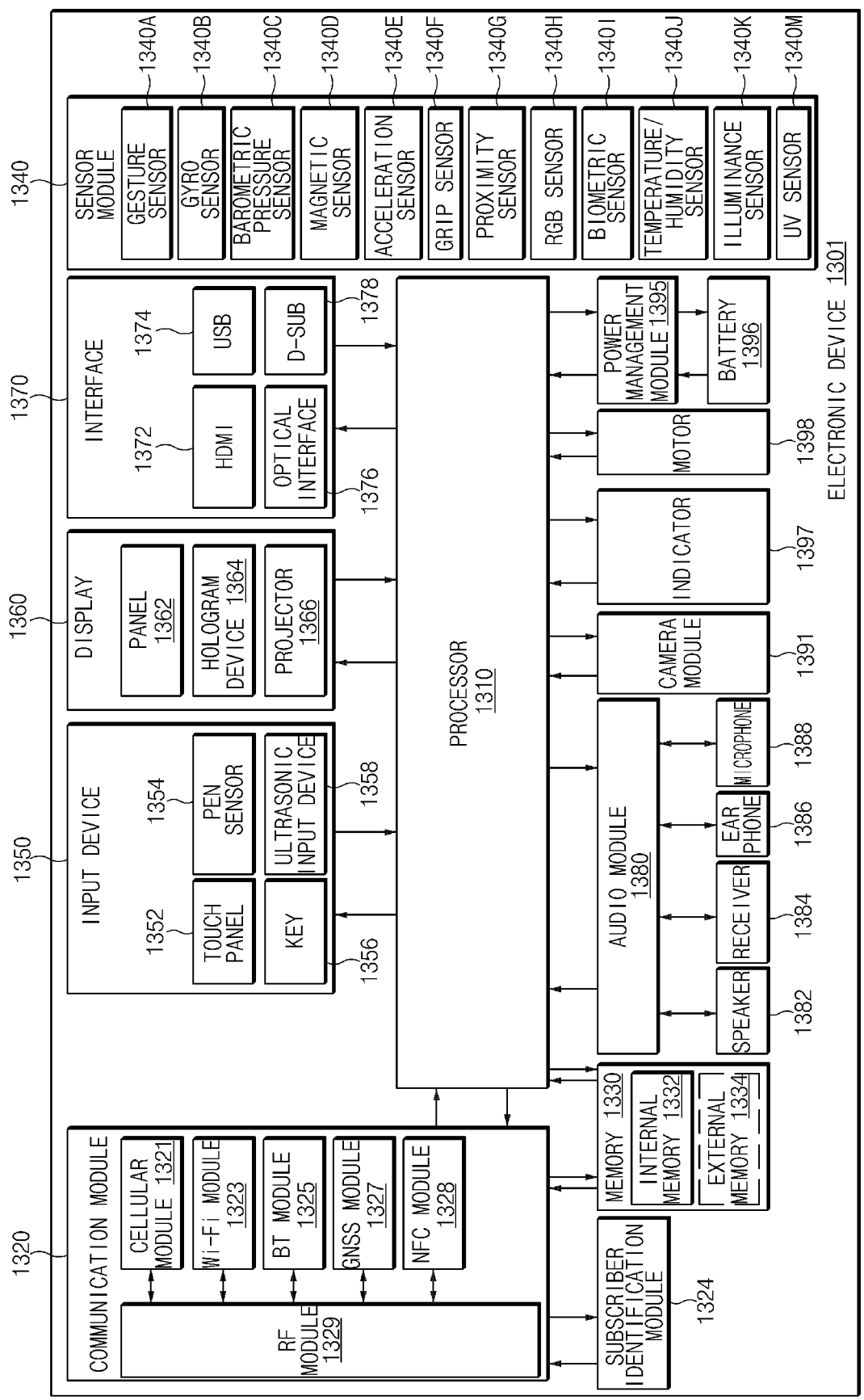
FIG. 13 is a block diagram illustrating an example electronic device, according to various example embodiments of the present disclosure.

FIG. 13 is a block diagram illustrating an example electronic device, according to various example embodiments.

An electronic device 1301 may include, for example, all or a part of an electronic device 1201 illustrated in FIG. 12. The electronic device 1301 may include one or more processors (e.g., an application processor (AP)) 1310, a communication module 1320, a subscriber identification module 1324, a memory 1330, a sensor module 1340, an input device 1350, a display 1360, an interface 1370, an audio module 1380, a camera module 1391, a power management module 1395, a battery 1396, an indicator 1397, and a motor 1398.

The processor 1310 may drive an operating system (OS) or an application program to control a plurality of hardware or software elements connected to the processor 1310 and may process and compute a variety of data. The processor 1310 may be implemented with a System on Chip (SoC), for example. According to an embodiment, the processor 1310 may further include a graphic processing unit (GPU) and/or an image signal processor. The processor 1310 may include at least a part (e.g., a cellular module 1321) of elements illustrated in FIG. 13. The processor 1310 may load and process an instruction or data, which is received from at least one of other elements (e.g., a nonvolatile memory) and may store result data in a nonvolatile memory.

The communication module 1320 may be configured the same as or similar to a communication interface 1270. For example, the communication module 1320 may include various communication circuitry, such as, for example, and without limitation, a cellular module 1321, a wireless-fidelity (Wi-Fi) module 1323, a Bluetooth (BT) module 1325, a global navigation satellite system (GNSS) module 1327, a near field communication (NFC) module 1328, and a radio frequency (RF) module 1329, or the like. The cellular module 1321 may provide voice communication, video communication, a character service, an Internet service, or the like through a communication network. According to an embodiment, the cellular module 1321 may perform discrimination and authentication of the electronic device 1301 within a communication network using a subscriber identification module 1324 (e.g., a SIM card), for example. According to an embodiment, the cellular module 1321 may perform at least a portion of functions that the processor 1310 provides. According to an embodiment, the cellular module 1321 may include a communication processor (CP). According to an embodiment, at least a part (e.g., two or more elements) of the cellular module 1321, the Wi-Fi module 1323, the BT module 1325, the GNSS module 1327, or the NFC module 1328 may be included within one Integrated Circuit (IC) or an IC package. The RF module 1329 may transmit and receive, for example, a communication signal (e.g., an RF signal). The RF module 1329 may include a transceiver, a power amplifier module (PAM), a frequency filter, a low noise amplifier (LNA), an antenna, or the like. According to various embodiments, at least one of the cellular module 1321, the Wi-Fi module 1323, the BT module 1325, the GNSS module 1327, or the NFC module 1328 may transmit and receive an RF signal through a separate RF module.

The subscriber identification module 1324 may include, for example, a card or an embedded SIM which includes a subscriber identification module and may include unique identification information (e.g., integrated circuit card identifier (ICCID)) or subscriber information (e.g., integrated mobile subscriber identity (IMSI)).

For example, the memory 1330 (e.g., the memory 1230) may include an internal memory 1332 and/or an external memory 1334. For example, the internal memory 1332 may include at least one of a volatile memory (e.g., a dynamic random access memory (DRAM), a static RAM (SRAM), a synchronous DRAM (SDRAM), or the like), a nonvolatile memory (e.g., a one-time programmable read only memory (OTPROM), a programmable ROM (PROM), an erasable and programmable ROM (EPROM), an electrically erasable and programmable ROM (EEPROM), a mask ROM, a flash ROM, a flash memory, a hard drive, or a solid state drive (SSD). The external memory 1334 may include a flash drive such as compact flash (CF), secure digital (SD), micro secure digital (Micro-SD), mini secure digital (Mini-SD), extreme digital (xD), a multimedia card (MMC), a memory stick, or the like. The external memory 1334 may be functionally or physically connected with the electronic device 1301 through various interfaces.

The sensor module 1340 may measure, for example, a physical quantity or may detect an operating state of the electronic device 1301. The sensor module 1140 may convert the measured or detected information to an electrical signal. The sensor module 1340 may include at least one of a gesture sensor 1340A, a gyro sensor 1340B, a barometric pressure sensor 1340C, a magnetic sensor 1340D, an acceleration sensor 1340E, a grip sensor 1340F, a proximity sensor 1340G, a color sensor 1340H (e.g., a red, green, blue (RGB) sensor), a living body (biometric) sensor 1340I, a temperature/humidity sensor 1340J, an illuminance sensor 1340K, or an UV sensor 1340M. Although not illustrated, additionally or generally, the sensor module 1340 may further include, for example, an e-nose sensor, an electromyography sensor (EMG) sensor, an electroencephalogram (EEG) sensor, an electrocardiogram (ECG) sensor, an infrared (IR) sensor, an iris sensor, and/or a fingerprint sensor. The sensor module 1340 may further include a control circuit that controls at least one or more sensors included therein. According to an embodiment, the electronic device 1301 may further include a processor which is a part of the processor 1310 or independent of the processor 1310 and is configured to control the sensor module 1340. The processor may control the sensor module 1340 while being in a sleep state.

The input device 1350 may include various input circuitry, such as, for example, and without limitation, a touch panel 1352, a (digital) pen sensor 1354, a key 1356, or an ultrasonic input device 1358, or the like. The touch panel 1352 may use at least one of capacitive, resistive, infrared and ultrasonic detecting methods. Also, the touch panel 1352 may further include a control circuit. The touch panel 1352 may further include a tactile layer to provide a tactile reaction to a user. The (digital) pen sensor 1354 may be, for example, a part of a touch panel or may include an additional sheet for recognition. The key 1356 may include, for example, a physical button, an optical key, a keypad, and the like. The ultrasonic input device 1358 may detect (or sense) an ultrasonic signal, which is generated from an input device, through a microphone (e.g., a microphone 1388) and may verify data corresponding to the detected ultrasonic signal.

The display 1360 (e.g., the display 1260) may include a panel 1362, a hologram device 1364, a projector 1366, and/or a control circuit that controls the panel 1362, the hologram device 1364, and the projector 1366. The panel 1362 may be implemented to be flexible, transparent or wearable, for example. The panel 1362 and the touch panel 1352 may be integrated into one or more modules. According to an embodiment, the panel 1362 may include a pressure sensor (or a "force sensor") that is capable of measuring the intensity of pressure on the touch of the user. The pressure sensor may be integrated with the touch panel 1352 or may be implemented with one or more sensors that are independent of the touch panel 1352. The hologram device 1364 may display a stereoscopic image in a space using a light interference phenomenon. The projector 1366 may project light onto a screen so as to display an image. The screen may be arranged inside or outside the electronic device 1301.

The interface 1370 may include various interface circuitry, such as, for example, and without limitation, a high-definition multimedia interface (HDMI) 1372, a universal serial bus (USB) 1374, an optical interface 1376, or a D-subminiature (D-sub) 1378, or the like. The interface 1370 may be included, for example, in the communication interface 1270 illustrated in FIG. 12. Additionally or alternatively, the interface 1370 may include, for example, a mobile high definition link (MHL) interface, a secure Digital (SD) card/multi-media card (MMC) interface, or an infrared data association (IrDA) standard interface.

The audio module 1380 may convert a sound and an electric signal in dual directions. At least a part of the audio module 1380 may be included, for example, in an input/output interface 1245 illustrated in FIG. 12. The audio module 1380 may process, for example, sound information that is input or output through a speaker 1382, a receiver 1384, an earphone 1386, or a microphone 1388. The camera module 1391 for shooting a still image or a video may include, for example, at least one image sensor (e.g., a front sensor or a rear sensor), a lens, an image signal processor (ISP), or a flash (e.g., an LED or a xenon lamp).

The power management module 1395 may manage, for example, power of the electronic device 1301. According to an embodiment, the power management module 1395 may include a power management integrated circuit (PMIC), a charger IC, or a battery or fuel gauge. The PMIC may have a wired charging method and/or a wireless charging method. The wireless charging method may include, for example, a magnetic resonance method, a magnetic induction method, or an electromagnetic method and may further include an additional circuit, for example, a coil loop, a resonant circuit, a rectifier, or the like. The battery gauge may measure, for example, a remaining capacity of the battery 1396 and a voltage, current or temperature thereof while the battery is charged. The battery 1396 may include, for example, a rechargeable battery and/or a solar battery.

The indicator 1397 may display a specific state of the electronic device 1301 or a part thereof (e.g., the processor 1310), such as a booting state, a message state, a charging state, and the like. The motor 1398 may convert an electrical signal into a mechanical vibration and may generate the following effects: vibration, haptic, and the like. For example, the electronic device 1301 may include a mobile TV supporting device that processes media data according to the standards of digital multimedia broadcasting (DMB), digital video broadcasting (DVB), MediaFlo™, or the like.

Each of the above-mentioned elements of the electronic device according to various embodiments of the present disclosure may be configured with one or more components, and the names of the elements may be changed according to the type of the electronic device. According to various embodiments, the electronic device (e.g., the electronic device 1301) may exclude some elements or may further include other additional elements. Alternatively, some of the elements of the electronic device may be combined with each other so as to form one entity, so that the functions of the elements may be performed in the same manner as before the combination.

Figure 14:
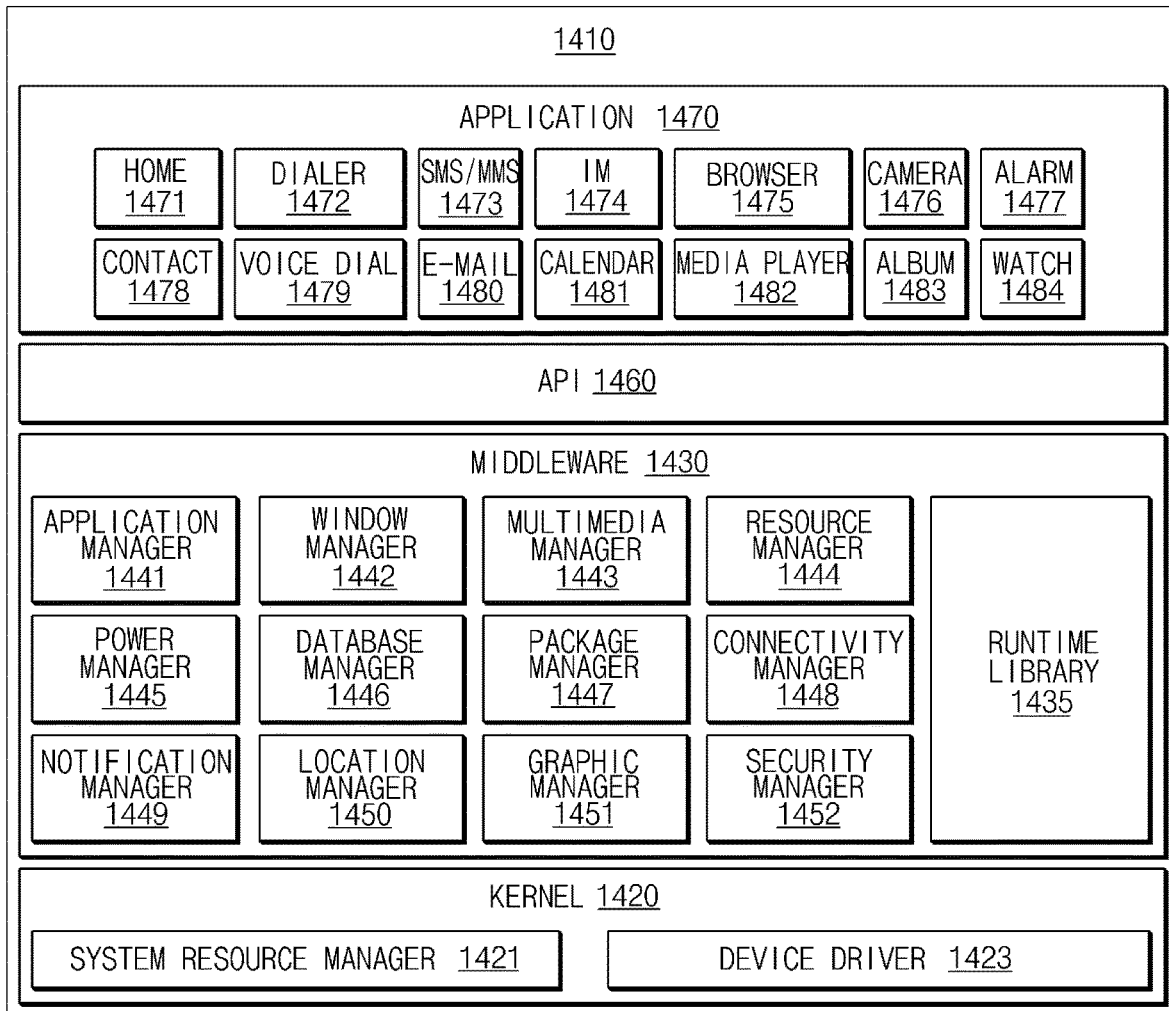
FIG. 14 is a block diagram illustrating an example program module according, to various example embodiments of the present disclosure.

FIG. 14 is a block diagram illustrating an example program module according to various example embodiments of the present disclosure.

According to an embodiment, a program module 1410 (e.g., the program 1240) may include an operating system (OS) to control resources associated with an electronic device (e.g., the electronic device 1201), and/or diverse applications (e.g., the application program 1247) driven on the OS. The OS may include, for example, Android™, iOS™, Windows™, Symbian™, Tizen™, or Bada™. Referring to FIG. 14, the program module 1410 may include a kernel 1420 (e.g., the kernel 1241), a middleware 1430 (e.g., the middleware 1243), an API 1460 (e.g., the API 1245), and/or an application 1470 (e.g., the application program 1247). At least a part of the program module 1410 may be preloaded on an electronic device or may be downloadable from an external electronic device (e.g., the first external electronic device 1202, the second external electronic device 1204, the server 1206, or the like).

The kernel 1420 may include, for example, a system resource manager 1421 and/or a device driver 1423. The system resource manager 1421 may perform control, allocation, or retrieval of system resources. According to an embodiment, the system resource manager 1421 may include a process managing unit, a memory managing unit, or a file system managing unit. The device driver 1423 may include, for example, a display driver, a camera driver, a Bluetooth driver, a common memory driver, an USB driver, a keypad driver, a Wi-Fi driver, an audio driver, or an inter-process communication (IPC) driver.

The middleware 1430 may provide, for example, a function which the application 1470 needs in common or may provide diverse functions to the application 1470 through the API 1460 to allow the application 1470 to use limited system resources of the electronic device. According to an embodiment, the middleware 1430 may include at least one of a runtime library 1435, an application manager 1441, a window manager 1442, a multimedia manager 1443, a resource manager 1444, a power manager 1445, a database manager 1446, a package manager 1447, a connectivity manager 1448, a notification manager 1449, a location manager 1450, a graphic manager 1451, or a security manager 1452.

The runtime library 1435 may include, for example, a library module, which is used by a compiler, to add a new function through a programming language while the application 1470 is being executed. The runtime library 1435 may perform input/output management, memory management, or processing of arithmetic functions. The application manager 1441 may manage, for example, the life cycle of the application 1470. The window manager 1442 may manage a GUI resource which is used in a screen. The multimedia manager 1443 may identify a format necessary to play media files, and may perform encoding or decoding of media files using a codec suitable for the format. The resource manager 1444 may manage source code of the application 1470 or a space of a memory. For example, the power manager 1445 may manage the capacity of a battery or power and may provide power information that is needed to operate an electronic device. According to an embodiment, the power manager 1445 may operate in conjunction with a basic input/output system (BIOS). For example, the database manager 1446 may generate, search for, or modify a database which is to be used in the application 1470. The package manager 1447 may install or update an application which is distributed in the form of a package file.

The connectivity manager 1448 may manage, for example, wireless connection. The notification manager 1449 may provide a user with an event such as an arrival message, an appointment, or a proximity notification. The location manager 1450 may manage, for example, location information of an electronic device. The graphic manager 1451 may manage, for example, a graphic effect to be provided to a user or a user interface relevant thereto. The security manager 1452 may provide, for example, system security or user authentication. According to an embodiment, the middleware 1430 may include a telephony manager, which manages a voice or video call function of the electronic device, or a middleware module that combines functions of the above-described elements. According to an embodiment, the middleware 1430 may provide a module specialized to each OS kind. The middleware 1430 may remove a part of the preexisting elements, dynamically, or may add new elements thereto.

The API 1460 may be, for example, a set of programming functions and may be provided with another configuration which is variable depending on an OS. For example, in the case where an OS is the android or iOS™, it may be permissible to provide one API set per platform. In the case where an OS is Tizen™, it may be permissible to provide two or more API sets per platform.

The application 1470 may include, for example, a home 1471, a dialer 1472, an SMS/MMS 1473, an instant message (IM) 1474, a browser 1475, a camera 1476, an alarm 1477, a contact 1478, a voice dial 1479, an e-mail 1480, a calendar 1481, a media player 1482, an album 1483, a watch 1484, or the like. Although not illustrated, various other applications may be included, such as, for example, and without limitation, an application related to health care (e.g., measuring an exercise quantity, blood sugar, or the like), or an application for offering environment information (e.g., atmospheric pressure, humidity, or temperature). According to an embodiment, the application 1470 may include an information exchanging application that supports information exchange between an electronic device and an external electronic device. The information exchanging application may include, for example, a notification relay application for transmitting specific information to the external electronic device, or a device management application for managing the external electronic device. For example, the notification relay application may send notification information, which is generated from other applications of an electronic device, to an external electronic device or may receive the notification information from the external electronic device and may provide a user with the notification information. The device management application may install, delete, or update, for example, a function (e.g., turn-on/turn-off of an external electronic device itself (or a part of components) or adjustment of brightness (or resolution) of a display) of the external electronic device, which communicates with an electronic device, or an application running in the external electronic device. According to an embodiment, the application 1470 may include an application (e.g., a health care application of a mobile medical device) that is assigned in accordance with an attribute of the external electronic device. According to an embodiment, the application 1470 may include an application received from an external electronic device. At least a part of the program module 1410 may be implemented (e.g., performed) by software, firmware, hardware (e.g., the processor 1310), or a combination of two or more thereof, and may include modules, programs, routines, sets of instructions, or processes for performing one or more functions.

The term "module" used herein may include a unit, which is implemented with hardware, software, or firmware, or any combination thereof, and may be interchangeably used with the terms "logic", "logical block", "component", "circuit", or the like. The "module" may be a minimum unit of an integrated component or a part thereof or may be a minimum unit for performing one or more functions or a part thereof. The "module" may be implemented mechanically or electronically and may include, for example, and without limitation, a dedicated processor, a CPU, an application-specific IC (ASIC) chip, a field-programmable gate array (FPGA), and a programmable-logic device, or the like, for performing some operations, which are known or will be developed.

According to various embodiments, at least a part of an apparatus (e.g., modules or functions thereof) or a method (e.g., operations) may be, for example, implemented by instructions stored in a computer-readable storage media (e.g., the memory 1230) in the form of a program module. The instruction, when executed by a processor (e.g., a processor 1220), may cause the processor and/or apparatus to perform a function corresponding to the instruction. The computer-readable recording medium may include a hard disk, a floppy disk, a magnetic media (e.g., a magnetic tape), an optical media (e.g., a compact disc read only memory (CD-ROM) and a digital versatile disc (DVD), a magneto-optical media (e.g., a floptical disk)), an embedded memory, and the like. The instruction may include codes created by a compiler or codes that are capable of being executed by a computer using an interpreter.

According to various embodiments, a module or a program module may include at least one of the above elements, or a part of the above elements may be omitted, or other elements may be further included. According to various embodiments, operations executed by modules, program modules, or other elements may be executed by a successive method, a parallel method, a repeated method, or a heuristic method, or at least one part of operations may be executed in different sequences or omitted. Alternatively, other operations may be added.

While the present disclosure has been illustrated and described with reference to various example embodiments thereof, it will be understood by those skilled in the art that various changes in form and details may be made therein without departing from the spirit and scope of the present disclosure as defined by the appended claims and their equivalents.

What is claimed is:

1. An electronic device comprising:
a memory configured to store profile information;
at least one first electrode;
at least one second electrode; and
a processor electrically connected to the at least one first electrode and the at least one second electrode,
wherein the processor is configured to:
determine a frequency of at least one among at least three signals for measuring body composition, based on the profile information;
output a synthesis signal to a body through the at least one first electrode, the synthesis signal being obtained by synthesizing the at least three signals, wherein the synthesis signal includes a signal corresponding to the determined frequency and the at least three signals each have different frequencies;
receive the synthesis signal passing through the body, through the at least one second electrode;
measure body impedance based on the received synthesis signal; and
determine the body composition based on the body impedance.

2. The electronic device of claim 1, wherein the profile information includes at least one of: height, age, weight, gender, exercise history, food intake history, sleep history, body composition measuring history, body state, and stress index.

3. The electronic device of claim 1, wherein the processor is configured to:
measure the body impedance for respective frequencies of the at least three signals.

4. The electronic device of claim 1, wherein the processor is configured to:

measure a skin contact impedance based on the synthesis signal; and remove the skin contact impedance from the body impedance.

5. The electronic device of claim 4, wherein the synthesis signal includes at least three first signals, each of the at least three first signals having different frequencies in a first frequency range, and at least three second signals, each of the at least three second signals having different frequencies in a second frequency range, the second frequency range being smaller than the first frequency range, and wherein the processor is configured to:

measure the skin contact impedance using the at least three second signals.

6. The electronic device of claim 1, wherein the processor is configured to:

generate at least three signals corresponding to the determined frequency; and generate the synthesis signal by synthesizing the at least three signals.

7. The electronic device of claim 6, wherein the processor is configured to:

adjust a phase of at least one among the at least three signals such that amplitude of the synthesis signal is minimized and/or reduced; and generate the synthesis signal using at least three signals, wherein the phase of each of the at least three signals is adjusted.

8. The electronic device of claim 1, wherein the memory is configured to store a plurality of synthesis signals obtained by synthesizing the at least three signals, each of the at least three signals having different frequencies, and wherein the processor is configured to:

verify a synthesis signal, including a signal corresponding to the determined frequency, from among the plurality of synthesis signals; and convert the verified synthesis signal to an analog signal.

9. The electronic device of claim 1, further comprising:

a display, wherein the processor is configured to:

verify a state based on the profile information; and display a user interface for providing notification that an error is to be included in the measured body composition in the display, if the state does not satisfy a specified standard.

10. The electronic device of claim 9, wherein the processor is configured to:

display a user interface providing notification that the state is a state suitable to measure the body composition in the display, if the state of the user satisfies the specified standard.

11. The electronic device of claim 1, wherein the processor is configured to:

store information about the measured body composition in the memory; and determine the frequency of at least one among the at least three signals based on the information about the body composition.

12. A body composition measuring method of an electronic device, the method comprising:

determining a frequency of at least one among at least three signals for measuring body composition, based on profile information;

outputting a synthesis signal to a body, the synthesis signal being obtained by synthesizing the at least three signals, wherein the synthesis signal includes a signal corresponding to the determined frequency and the at least three signals each having different frequencies;

measuring body impedance based on a received synthesis signal; and determining the body composition based on the body impedance.

13. The method of claim 12, wherein the profile information includes at least one of: height, age, weight, gender, exercise history, food intake history, sleep history, body composition measuring history, body state, and stress index.

14. The method of claim 12, wherein the measuring of the body impedance includes:

measuring the body impedance for respective frequencies of the at least three signals.

15. The method of claim 12, further comprising:

measuring a skin contact impedance based on the synthesis signal; and removing the skin contact impedance from the body impedance.

16. The method of claim 15, wherein the synthesis signal includes at least three first signals, each of the at least three first signals having different frequencies in a first frequency range, and at least three second signals, each of the at least three second signals having different frequencies in a second frequency range, the second frequency range being smaller than the first frequency range, and wherein the measuring of the skin contact impedance includes:

measuring the skin contact impedance using the at least three second signals.

17. The method of claim 12, wherein the outputting of the synthesis signal to the body includes:

generating at least three signals corresponding to the determined frequency;

generating the synthesis signal obtained by synthesizing the at least three signals; and outputting the generated synthesis signal to the body.

18. The method of claim 17, further comprising:

adjusting a phase of at least one among the at least three signals such that amplitude of the synthesis signal is minimized and/or reduced.

19. The method of claim 12, wherein the outputting of the synthesis signal to the body includes:

verifying the synthesis signal, which includes the signal corresponding to the determined frequency, from among a plurality of synthesis signals stored in a memory;

converting the verified synthesis signal into an analog signal; and outputting the synthesis signal converted into the analog signal to the body.

20. A non-transitory computer-readable recording medium having recorded thereon a program which when executed by a processor causes an electronic apparatus to perform operations comprising:

determining a frequency of at least one among at least three signals for measuring body composition, based on profile information;

outputting a synthesis signal to a body, the synthesis signal being obtained by synthesizing the at least three signals, wherein the synthesis signal includes a signal corresponding to the determined frequency and the at least three signals each having different frequencies;

receiving the synthesis signal;

measuring body impedance based on the received synthesis signal; and determining the body composition based on the body impedance.

\* \* \* \* \*